(12) United States Patent
Butler et al.

(10) Patent No.: US 12,048,634 B2
(45) Date of Patent: Jul. 30, 2024

(54) RADIALLY EXPANDABLE SPINAL INTERBODY DEVICE AND IMPLANTATION TOOL

(71) Applicant: Life Spine, Inc., Huntley, IL (US)

(72) Inventors: Michael S. Butler, St. Charles, IL (US); Daniel Predick, West Lafayette, IN (US); Alexander Allen Salinas, Yorkville, IL (US)

(73) Assignee: Life Spine, Inc., Huntley, IL (US)

( * ) Notice: Subject to any disclaimer, the term of this patent is extended or adjusted under 35 U.S.C. 154(b) by 331 days.

(21) Appl. No.: 17/679,494

(22) Filed: Feb. 24, 2022

(65) Prior Publication Data

US 2022/0249247 A1    Aug. 11, 2022

Related U.S. Application Data

(63) Continuation of application No. 16/378,437, filed on Apr. 8, 2019, now Pat. No. 11,298,241, which is a
(Continued)

(51) Int. Cl.
*A61F 2/44*        (2006.01)
*A61B 6/12*        (2006.01)
(Continued)

(52) U.S. Cl.
CPC .............. *A61F 2/4465* (2013.01); *A61B 6/12* (2013.01); *A61F 2/4611* (2013.01);
(Continued)

(58) Field of Classification Search
CPC .................. A61F 2/4465; A61F 2/4611; A61F 2002/3008; A61F 2002/30126;
(Continued)

(56) References Cited

U.S. PATENT DOCUMENTS 4,636,217 A   1/1987 Ogilvie et al.
5,390,683 A   2/1995 Pisharodi
(Continued)

FOREIGN PATENT DOCUMENTS

WO    WO-2006/105437 A2   10/2006
WO    WO-2012/007918 A2    1/2012

OTHER PUBLICATIONS

Bacfuse® Spinous Process Fusion Plate Surgical Technique, 2011, Pioneer Surgical, 12 pages.
(Continued)

*Primary Examiner* — Nicholas J Plionis
(74) *Attorney, Agent, or Firm* — Foley & Lardner LLP

(57) ABSTRACT

A spinal interbody device includes a base link comprising a first end and a second end, the base link including a cutout extending through the base link between the first end and the second end; a linkage including a first link having a first end coupled to the first end of the base link and a second end, the first link including a first aperture extending through the first link and defining a first longitudinal axis; and a second link having a first end coupled to the second end of the first link and a second end coupled to the second end of the base link, the second link including a second aperture extending through the second link and defining a second longitudinal axis. The base link and the first and second links define top and bottom surfaces configured to engage adjacent portions of bone, and first and second sides extending between the top and bottom surfaces. When the linkage is movable relative to the base link between a collapsed position and an expanded position, wherein when in the expanded position, an unobstructed line of sight is provided through the cutout and the first aperture along the first longitudinal axis and through the cutout and the second aperture along the second longitudinal axis.

20 Claims, 22 Drawing Sheets

Related U.S. Application Data continuation-in-part of application No. 15/477,293, filed on Apr. 3, 2017, now Pat. No. 10,251,759, which is a continuation-in-part of application No. 14/829,122, filed on Aug. 18, 2015, now Pat. No. 9,610,172, which is a continuation-in-part of application No. 13/585,521, filed on Aug. 14, 2012, now Pat. No. 9,138,328, which is a continuation-in-part of application No. 12/079,737, filed on Mar. 28, 2008, now Pat. No. 8,241,358.

(60) Provisional application No. 60/920,766, filed on Mar. 29, 2007.

(51) Int. Cl.
*A61F 2/30* (2006.01)
*A61F 2/46* (2006.01)

(52) U.S. Cl.
CPC ............ *A61F 2002/3008* (2013.01); *A61F 2002/30126* (2013.01); *A61F 2002/30471* (2013.01); *A61F 2002/3055* (2013.01); *A61F 2002/30556* (2013.01); *A61F 2002/30579* (2013.01); *A61F 2002/30593* (2013.01); *A61F 2002/30904* (2013.01); *A61F 2002/4627* (2013.01)

(58) Field of Classification Search
CPC .. A61F 2002/30471; A61F 2002/30556; A61F 2002/30579; A61F 2002/30593; A61F 2002/4627; A61B 6/12
See application file for complete search history.

(56) References Cited

U.S. PATENT DOCUMENTS

| | | |
|---|---|---|
| 5,658,335 A | 8/1997 | Allen |
| 5,658,337 A | 8/1997 | Kohrs et al. |
| 5,836,948 A | 11/1998 | Zucherman et al. |
| 5,860,977 A | 1/1999 | Zucherman et al. |
| 5,876,404 A | 3/1999 | Zucherman et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,126,689 A | 10/2000 | Brett |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,375,682 B1 | 4/2002 | Fleischmann et al. |
| 6,409,766 B1 | 6/2002 | Brett |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,648,917 B2 | 11/2003 | Gerbec et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,723,097 B2 | 4/2004 | Fraser et al. |
| 6,773,460 B2 | 8/2004 | Jackson |
| 6,796,983 B1 | 9/2004 | Zucherman et al. |
| 7,018,413 B2 | 3/2006 | Kruger |
| 7,087,055 B2 | 8/2006 | Lim et al. |
| 7,101,375 B2 | 9/2006 | Zucherman et al. |
| 7,695,513 B2 | 4/2010 | Zucherman et al. |
| 9,034,041 B2 | 5/2015 | Wolters et al. |
| 9,044,342 B2 | 6/2015 | Perloff et al. |
| 9,278,008 B2 | 3/2016 | Perloff et al. |
| 9,468,466 B1 | 10/2016 | Shenoy et al. |
| 9,655,737 B2 | 5/2017 | Perloff et al. |
| 9,877,759 B2 | 1/2018 | Predick |
| 9,980,822 B2 | 5/2018 | Perloff et al. |
| 10,085,844 B2 | 10/2018 | Perloff et al. |
| 10,117,691 B2 | 11/2018 | Predick |
| 2004/0073312 A1 | 4/2004 | Eisermann et al. |
| 2004/0127993 A1 | 7/2004 | Kast et al. |
| 2004/0153156 A1 | 8/2004 | Cohen et al. |
| 2004/0167625 A1 | 8/2004 | Beyar et al. |
| 2004/0249466 A1 | 12/2004 | Liu et al. |
| 2005/0033437 A1 | 2/2005 | Bao et al. |
| 2005/0043800 A1 | 2/2005 | Paul et al. |
| 2005/0113920 A1 | 5/2005 | Foley et al. |
| 2005/0131536 A1 | 6/2005 | Eisermann et al. |
| 2005/0143827 A1 | 6/2005 | Globerman et al. |
| 2005/0228391 A1 | 10/2005 | Levy et al. |
| 2006/0036258 A1 | 2/2006 | Zucherman et al. |
| 2006/0089642 A1 | 4/2006 | Diaz et al. |
| 2006/0095136 A1 | 5/2006 | McLuen |
| 2006/0142858 A1* | 6/2006 | Colleran ............... A61F 2/4465 623/17.11 |
| 2006/0189999 A1 | 8/2006 | Zwirkoski |
| 2006/0224241 A1 | 10/2006 | Butler et al. |
| 2006/0264938 A1 | 11/2006 | Zucherman et al. |
| 2007/0142915 A1 | 6/2007 | Altarac et al. |
| 2008/0140207 A1 | 6/2008 | Olmos et al. |
| 2008/0161818 A1 | 7/2008 | Kloss et al. |
| 2008/0177391 A1 | 7/2008 | Mitchell et al. |
| 2008/0312741 A1 | 12/2008 | Lee et al. |
| 2010/0113939 A1 | 5/2010 | Mashimo et al. |
| 2011/0112642 A1 | 5/2011 | Tohmeh |
| 2011/0218631 A1 | 9/2011 | Woodburn et al. |
| 2011/0282453 A1 | 11/2011 | Greenhalgh et al. |
| 2013/0041471 A1 | 2/2013 | Siegal et al. |
| 2013/0079883 A1 | 3/2013 | Butler et al. |
| 2013/0085572 A1 | 4/2013 | Glerum et al. |
| 2013/0103156 A1 | 4/2013 | Packer et al. |
| 2014/0148904 A1 | 5/2014 | Robinson |
| 2014/0277473 A1 | 9/2014 | Perrow |
| 2015/0223946 A1 | 8/2015 | Weiman et al. |
| 2016/0256291 A1 | 9/2016 | Miller |
| 2017/0172758 A1* | 6/2017 | Field ..................... A61F 2/4455 |

OTHER PUBLICATIONS

International Preliminary Report on Patentability and Written Opinion for PCT/US2008/004050, Sep. 29, 2009, 7 pages.

International Preliminary Report on Patentability for International Application No. PCT/US06/12060 mailing date Sep. 30, 2007, 3 pages.

International Search Report and Written Opinion for International Application No. PCT/US06/12060, mailing date Apr. 5, 2007, 3 pages.

International Search Report and Written Opinion for PCT/US08/004050, mailed Jul. 21, 2008, 10 pages.

International Search Report and Written Opinion for PCT/US08/04050, mailed Jul. 21, 2008, 10 pages.

International Search Report for Application No. PCT/US06/12060, date of mailing Apr. 5, 2007, 1 page.

\* cited by examiner

RADIALLY EXPANDABLE SPINAL INTERBODY DEVICE AND IMPLANTATION TOOL

CROSS-REFERENCE TO RELATED PATENT APPLICATIONS

This application is a continuation of U.S. application Ser. No. 16/378,437, filed Apr. 8, 2019, which is a continuation-in-part of U.S. application Ser. No. 15/477,293, filed Apr. 3, 2017, now U.S. Pat. No. 10,251,759, which is a continuation-in-part of U.S. application Ser. No. 14/829,122, filed Aug. 18, 2015, now U.S. Pat. No. 9,610,172, which is a continuation-in-part of U.S. application Ser. No. 13/585,521, filed Aug. 14, 2012, now U.S. Pat. No. 9,138,328, which is a continuation-in-part of U.S. application Ser. No. 12/079,737, filed Mar. 28, 2008, now U.S. Pat. No. 8,241,358, which claims the benefit of U.S. Provisional Patent Application No. 60/920,766, filed Mar. 29, 2007. The entire contents of all of these applications are incorporated herein by reference.

BACKGROUND

The present invention relates to spinal interbody devices for implantation between a pair of adjacent vertebrae for providing support to the adjacent vertebrae for fusion thereof and, more particularly, to expandable interbody devices for implantation between a pair of adjacent vertebrae for providing support to the adjacent vertebrae for fusion thereof.

The disc between vertebrae of a human spine may become damaged due to disease, injury, stress, deterioration because of age or otherwise, or due to a congenital defect. In some instances vertebrae may become compressed against a disc or otherwise become damaged. The spine may thereby become misaligned. In these and other cases the vertebrae can become too closely spaced anteriorly which causes an undesired abnormal curvature of the spine with respect to lordosis or kyphosis. Other deformations and/or problems may occur.

In these cases and more, spinal fusion surgery may be utilized to join or fuse two or more vertebrae together. Fusion surgeries typically require the use of bone graft to facilitate fusion. This involves taking small amounts of bone from the patient's pelvic bone (autograft), or from a donor (allograft), and then packing it between the vertebrae in order to "fuse" them together. This bone graft is typically packed into a biomechanical spacer implant, spinal prosthesis or interbody device, which will take the place of the intervertebral disc which is entirely removed in the surgical process. Spinal fusion surgery is a common treatment for such spinal disorders as spondylolisthesis, scoliosis, severe disc degeneration, or spinal fractures. Three common fusion surgeries are 1) Posterior Lumbar Interbody Fusion or PLIF; 2) Anterior Lumbar Interbody Fusion or ALIF; and 3) Transforaminal Lumbar Interbody Fusion (TLIF).

In the PLIF technique, the vertebrae are reached through an incision in the patient's back (posterior). The PLIF procedure involves three basic steps. One is pre-operative planning and templating including use of MRI and CAT scans to determine what size implant(s) the patient needs. Two is preparing the disc space. Depending on the number of levels to be fused, a 3-6 inch incision is made in the patient's back and the spinal muscles are retracted (or separated) to allow access to the vertebral disc. The surgeon then removes some or all of the affected disc and surrounding tissue. Third is insertion of the implant(s). Once the disc space is prepared, bone graft, allograft or BMP with a biomechanical spacer implant, is inserted into the disc space to promote fusion between the vertebrae. Additional instrumentation (such as rods or screws) may also be used to further stabilize the spine.

The TLIF technique is a refinement of the PLIF procedure and is used as a surgical treatment for conditions typically affecting the lumbar spine. The TLIF technique involves approaching the spine in a similar manner as the PLIF approach but more from the side of the spinal canal through a midline incision in the patient's back. This approach greatly reduces the amount of surgical muscle dissection and minimizes the nerve manipulation required to access the vertebrae, discs and nerves. The TLIF approach allows for minimal access and endoscopic techniques to be used for spinal fusion. Disc material is removed from the spine and replaced with bone graft (along with cages, screws, or rods if necessary) inserted into the disc space. The instrumentation helps facilitate fusion while adding strength and stability to the spine.

The ALIF procedure is similar to PLIF procedure; however, the ALIF procedure is done from the front (anterior) of the body, usually through a 3-5 inch incision in the lower left lower abdominal area. This incision may involve cutting through, and later repairing, the muscles in the lower abdomen. This technique also lends itself to a mini open approach that preserves the muscles and allows access to the front of the spine through a very small incision and use of endoscopic technology. This approach maintains abdominal muscle strength and function. It is therefore oftentimes used to fuse the L5-S1 disc space. As such, it can be appreciated that the smaller the interbody device the better.

When interbody devices are used, it is desirable for them to engage as much surface of the bone of the vertebrae as possible to provide support to the vertebral bone and to thereby reduce the likelihood of subsidence of the device into the bone resulting from contact pressure of the interbody device against bone surfaces. Subsidence can occur since part of the bone is somewhat spongy in nature, especially near the centers of the adjacent vertebrae.

The structure of interbody devices mainly functions to support the two adjacent vertebral surfaces, unless the interbody device is also used as a fusion cage within or around which to pack bone fusion material. Because it is also desirable in such structures to maintain weight and volume as low as possible in order to make the device more compatible with the body, it is also desirable to make the interbody device as small and lightweight as possible, while still maintaining strength.

Accordingly, there presently exists a need for improved interbody devices.

SUMMARY

The present invention is a radially expandable spinal interbody device for implantation between adjacent vertebrae of a spine. The radially expandable interbody device is deliverable to an implant area in a radially collapsed state having minimum radial dimensions and once positioned is then radially expandable through and up to maximum radial dimensions. The expanded radially expandable spinal interbody device is configured to closely mimic the anatomical configuration of a vertebral face.

The radially expandable spinal interbody device is formed of arced, pivoting linkages that allow transfiguration from the radially collapsed minimum radial dimensions through and up to the radially expanded maximum radial dimensions once deployed at the implant site (i.e. between adjacent vertebrae). The pivoting linkages have ends with locking features that inhibit or prevent overextension of the linkages. In one form of the locking features, one end of the linkage includes lobes that form a pocket while the other end of the linkage includes a projection that is adapted to be received in the pocket of the lobes of an adjacent linkage.

In one form, the radially expandable spinal interbody device utilizes two like linkages that are pivotally connected to one another at opposite ends thereof. Each linkage is preferably, but not necessarily, formed of two pivotally connected arced links. The links each have serrations or teeth on upper and lower surfaces. The links are connected via pivot pins that also provide markers when formed of a radio opaque material such as tantalum.

The radially expandable spinal interbody device is made from a bio-compatible material such as titanium, a titanium alloy, stainless steel, other metal, polymer, composite, ceramic or a combination thereof as appropriate. The radially expandable interbody device 10 is preferably, but not necessarily, used as a lumbar interbody device and/or for use in ALIF surgery.

A surgical tool is provided for positioning and deploying the radially expandable interbody device/implant. The surgical tool has a positioning portion adapted to releasably attach to the radially expandable interbody device and a deployment portion movably retained by the positioning portion and adapted to deploy the radially expandable interbody device. The deployment portion is also adapted to introduce bone graft, BMP or the like into the radially expandable interbody device.

Releasable attachment to the radially expandable interbody device is accomplished in one form through multi-directional installation threads of a bore of each link. Since each link includes a threaded bore, various rotational orientations may be achieved during implantation.

Some embodiments are directed to a spinal interbody device comprising a base link having a first end and a second end; a linkage comprising a first link having a first end coupled to the first end of the base link and a second end; a second link having a first end coupled to the second end of the first link and a second end coupled to the second end of the base link; and an adjustment screw provided in the second end of the base link and configured to engage the second end of the second link to move the linkage between a collapsed position and an expanded position.

Another embodiment is directed to a spinal interbody device comprising a first link; a second link pivotally coupled to the first link; a third link having a first end and a second end, wherein the first link is coupled to the first end and configured to pivot and translate relative to the third link, wherein the second link is coupled to the second end and configured to move only in a pivoting fashion relative to the third link; wherein the second end of the third link is configured to engage a projection of the second link.

Another embodiment is directed to a spinal interbody device comprising a unitary base link having a first end and a second end, the first end having a first channel defined by a wall having a slot, the second end having a second channel defined by a pair of walls with apertures therein; a first link having a projection extending into the first channel of the base link; a second link pivotally coupled to the first link, the second link having a projection extending into the second channel of the base link; wherein the first link pivots and translates relative to the base link, and the second link moves only pivotally relative to the base link; wherein the first and second links are configured to move between a collapsed position and an expanded position.

Another embodiment relates to a spinal interbody device comprising a base link having a first end and a second end; a linkage comprising a first link having a first end coupled to the first end of the base link and a second end; and a second link having a first end coupled to the second end of the first link and a second end coupled to the second end of the base link; wherein the base link and the first and second links define top and bottom surfaces configured to engage adjacent portions of bone, and first and second sides extending between the top and bottom surfaces; and at least one radiographic element provided in at least one of the first link and the second link and positioned such that the radiographic element provides an indication of a degree of expansion of the device when the device is imaged from one of the first side and the second side of the device.

Another embodiment relates to a method of implanting an expandable device, comprising positioning an expandable device including an imaging element in a desired location; positioning am imaging device at a predetermined orientation relative to the expandable device; adjusting the expandable device to a first degree of expansion; acquiring an image portion of the imaging element; determining a degree of expansion of the device based on the image portion; and adjusting the expandable device to a second degree of expansion.

Another embodiment relates to a method of implanting an expandable device, comprising positioning an expandable device in a desired position between adjacent portions of bone, wherein the device includes top and bottom surfaces, and first and second sides extending between the top and bottom surfaces, wherein the device further includes an imaging element extending along a plane generally bisecting the device between the top and bottom surfaces; positioning an imaging device at a perspective generally perpendicular to one of the first and second sides; acquiring an image portion of the imaging element; and determining a degree of expansion of the device based on the image portion.

Another embodiment relates to a spinal interbody device including a base link having a first end and a second end; a linkage including a first link having a first end coupled to the first end of the base link and a second end; and a second link having a first end coupled to the second end of the first link and a second end coupled to the second end of the base link; wherein the base link and the first and second links define top and bottom surfaces configured to engage adjacent portions of bone, and first and second sides extending between the top and bottom surfaces; and at least one imaging element provided in at least one of the first link and the second link and positioned such that the imaging element provides an indication of a degree of expansion of the device when the device is imaged from one of the first side and the second side of the device.

Another embodiment relates to a method of implanting an expandable device, including positioning an expandable device including an imaging element in a desired location; positioning an imaging device at a predetermined orientation relative to the expandable device; adjusting the expandable device to a first degree of expansion; acquiring an image portion of the imaging element using the imaging device; determining a degree of expansion of the device based on the image portion; and adjusting the expandable device to a second degree of expansion.

Another embodiment relates to a spinal interbody device including a base link comprising a first end and a second end, the base link including a cutout extending through the base link between the first end and the second end; a linkage including a first link having a first end coupled to the first end of the base link and a second end, the first link including a first aperture extending through the first link and defining a first longitudinal axis; and a second link having a first end coupled to the second end of the first link and a second end coupled to the second end of the base link, the second link including a second aperture extending through the second link and defining a second longitudinal axis; wherein the base link and the first and second links define top and bottom surfaces configured to engage adjacent portions of bone, and first and second sides extending between the top and bottom surfaces; and wherein when the linkage is movable relative to the base link between a collapsed position and an expanded position, wherein when in the expanded position, an unobstructed line of sight is provided through the cutout and the first aperture along the first longitudinal axis and through the cutout and the second aperture along the second longitudinal axis.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

Like reference numerals indicate the same or similar parts throughout the several figures.

A full dissertation of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Referring to the Figures and in particular FIGS. 1-6, there is depicted an exemplary embodiment of a radially expandable interbody device, spinal prosthesis or the like generally designated 10 fashioned in accordance with the present principles. The radially expandable interbody device 10 is configured to be delivered to an implant site in a radially collapsed state or with radially minimal dimensions 200 (see, e.g., FIG. 8) and then radially expanded or with radially maximum dimensions 300 at the implant site (see, e.g., FIG. 9) hence the term expandable or dynamic. In this manner, the radially expandable interbody device 10 may be delivered to the implant site through a small delivery area when in the radially collapsed state and then easily radially expanded when implanted. The radially expandable interbody device 10 may be fashioned from a biocompatible material such as titanium, a titanium alloy, stainless steel, other metal, polymer, composite, ceramic and/or any combination thereof. The radially expandable interbody device 10 is preferably, but not necessarily, used as a lumbar interbody device and/or for use in an ALIF surgery.

Figure 1:
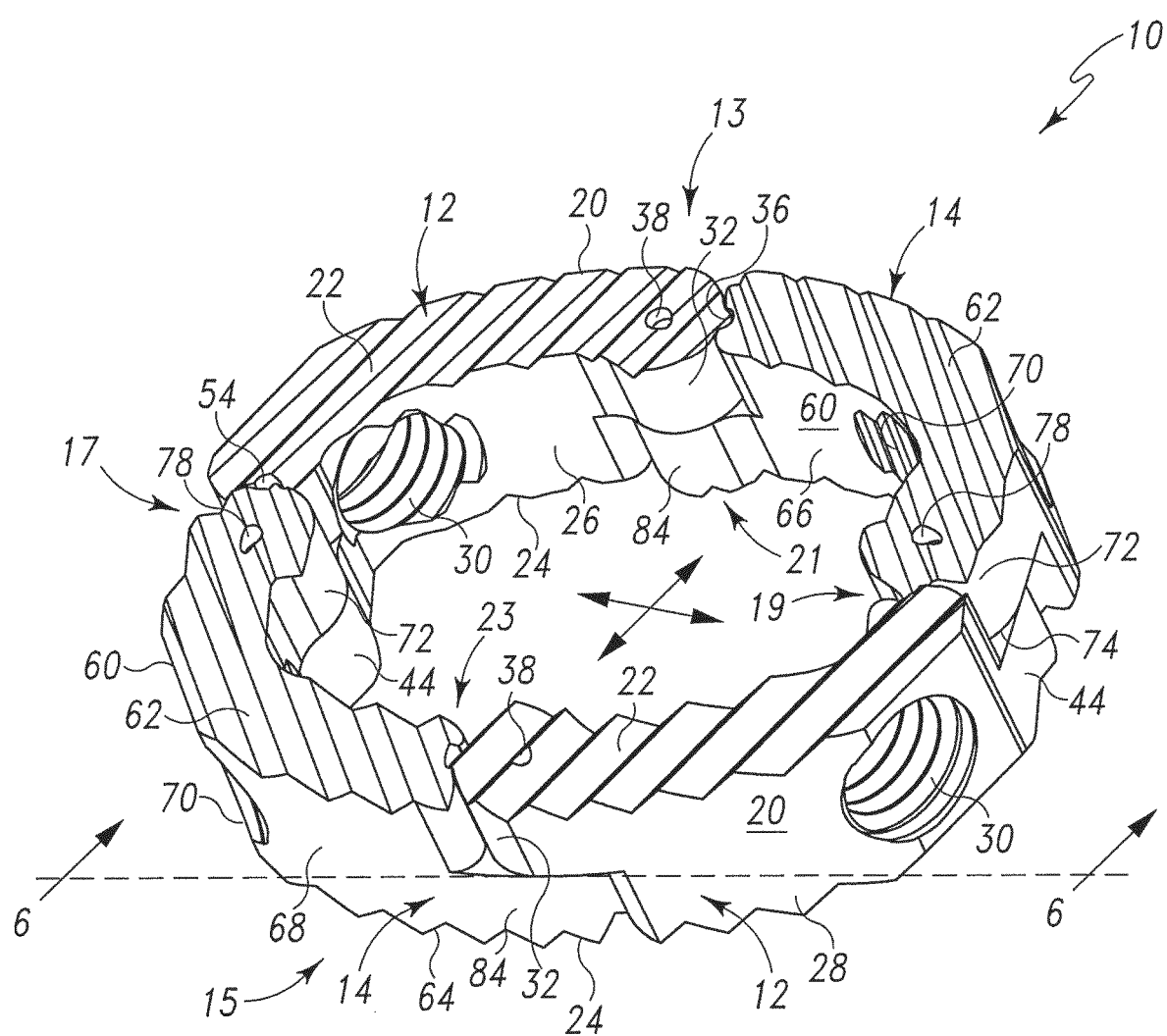
FIG. 1 is a perspective view of an exemplary embodiment of a radially expandable spinal interbody device fashioned in accordance with the present principles.
Figure 2:
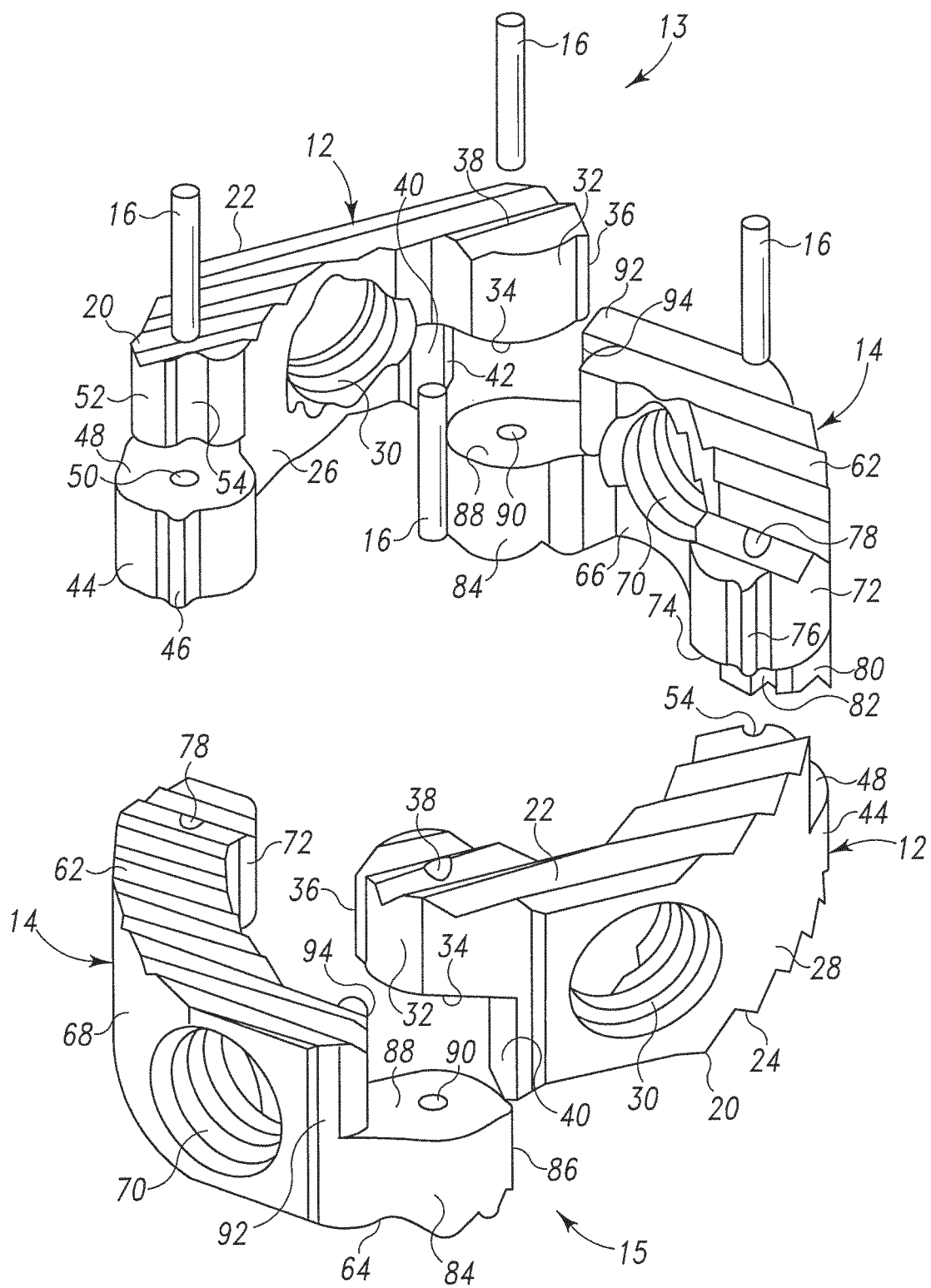
FIG. 2 is an exploded view of the components of the radially expandable spinal interbody device of FIG. 1.
Figure 3:
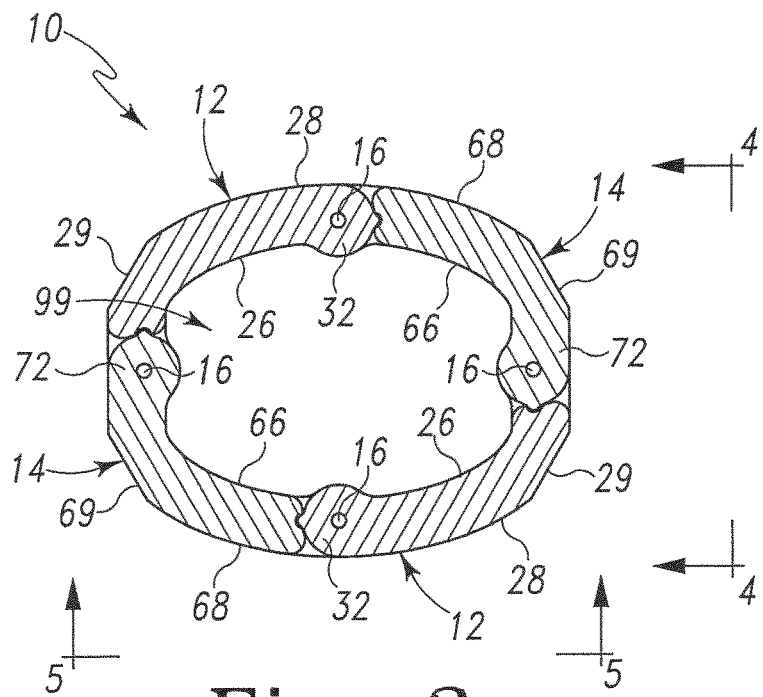
FIG. 3 is a top view of the radially expandable spinal interbody device of FIG. 1.
Figure 8:
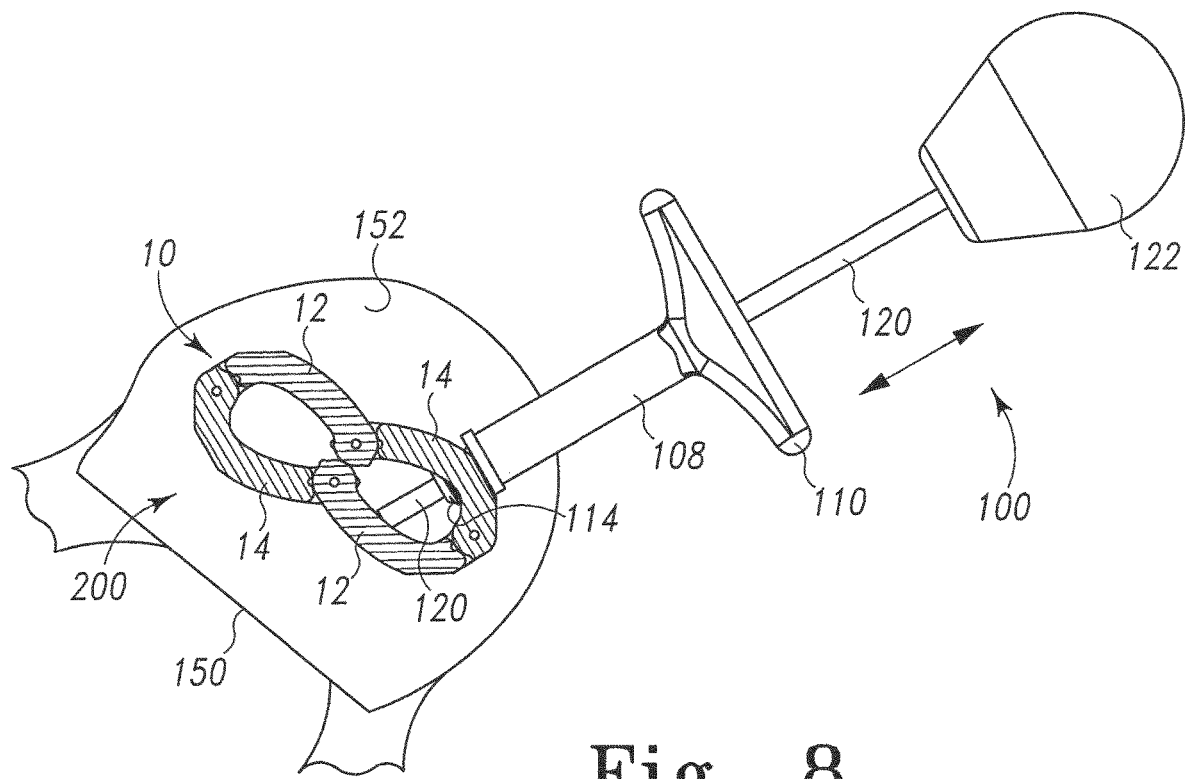
FIG. 8 is an illustration of a stage in a method of use of the radially expandable spinal interbody device of FIG. 1 utilizing the implantation and deployment device of FIG. 7 wherein the radially expandable spinal interbody device is in a pre-expanded or collapsed state adjacent a vertebra.
Figure 9:
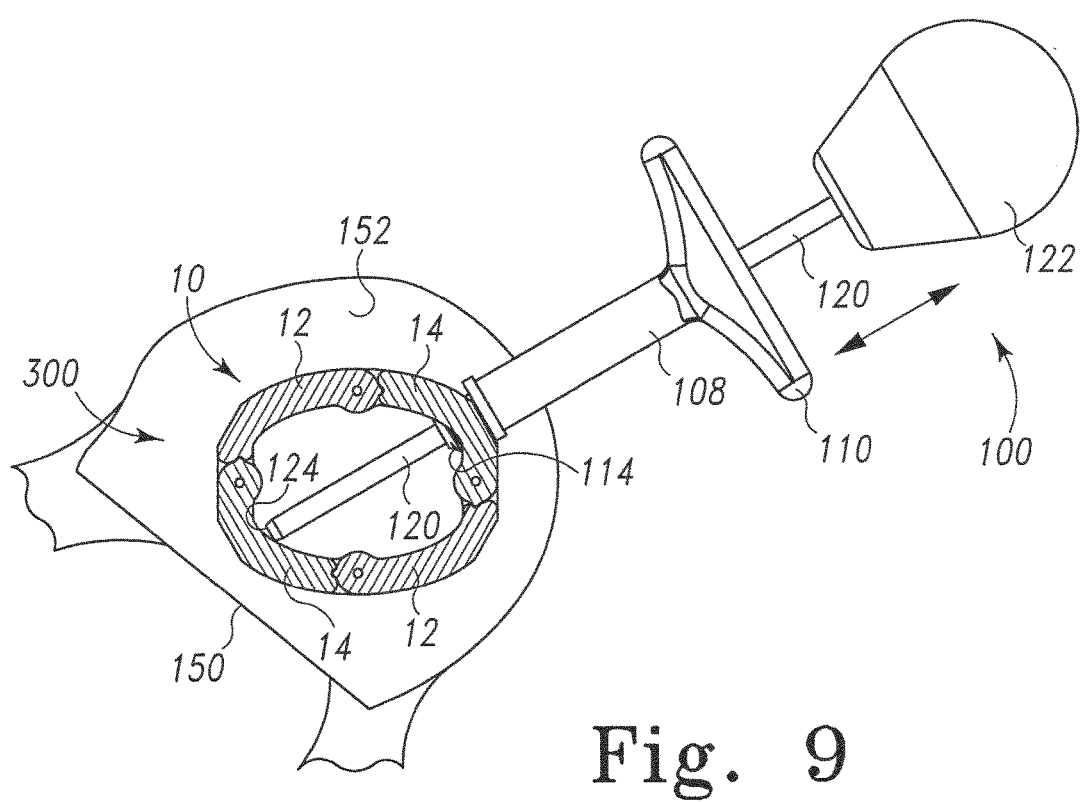
FIG. 9 is an illustration of another stage in the method of use of the radially expandable spinal interbody device of FIG. 1 utilizing the implantation and deployment device of FIG. 7 wherein the radially expandable spinal interbody device is in an expanded or un-collapsed state adjacent the vertebra.
Figure 10:
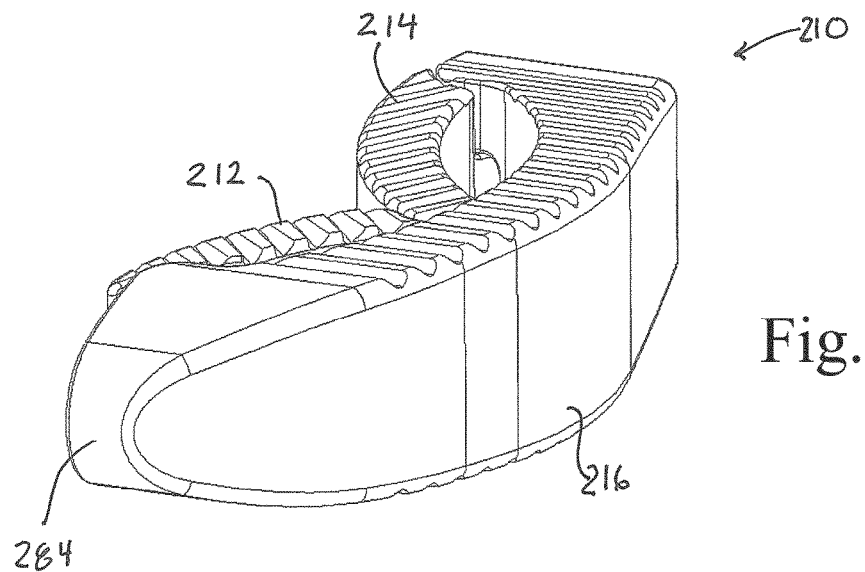
FIG. 10 is a perspective view of a radially expandable spinal interbody device according to another exemplary embodiment.
Figure 11:
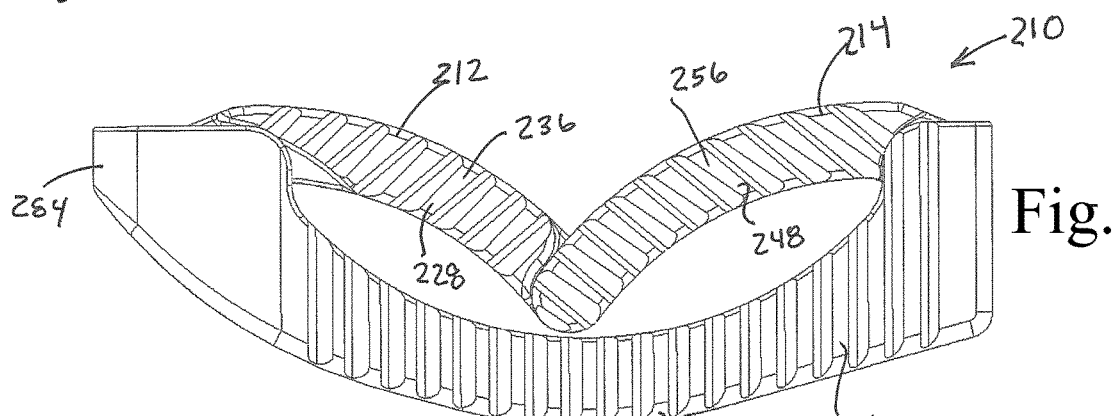
FIG. 11 is a top view of the device of FIG. 10 in a radially collapsed configuration according to an exemplary embodiment.
Figure 12:
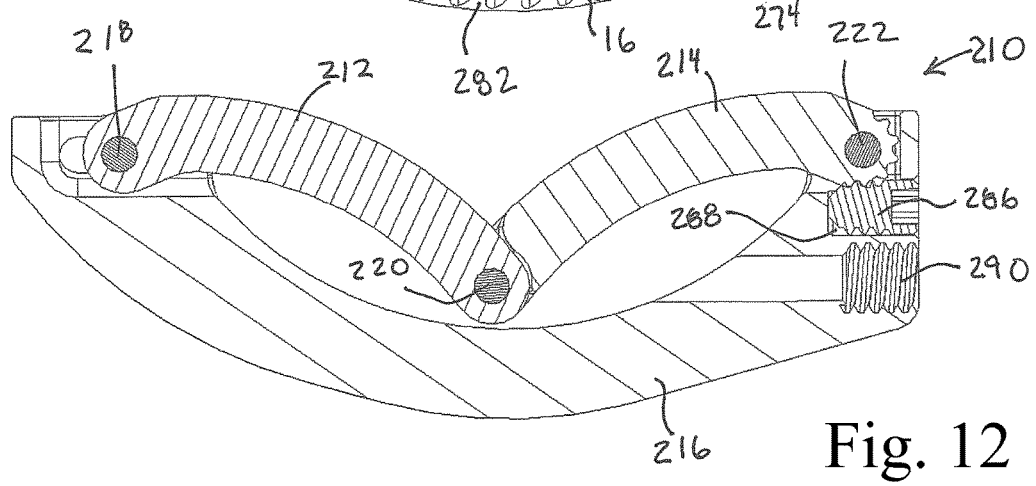
FIG. 12 is a cross-sectional view of the device of FIG. 11 according to an exemplary embodiment.

The radially expandable interbody device 10 is defined by a first linkage 13 that is coupled to a second linkage 15. The first linkage 13 is radially pivotally coupled to the second linkage 15 at first ends thereof to define a first radial pivot junction or juncture 17, and at second ends thereof to define a second radial pivot junction or juncture 19. The first linkage 13 is defined by a first pair of links 12 and 14, while the second linkage 15 is defined a second pair of identical links 12 and 14. The first and second links 12 and 14 of the first linkage 13 are radially pivotally connected to one another to define a third radial pivot junction or juncture 21. Likewise, the first and second links 12 and 14 of the second linkage 15 are pivotally connected to one another to define a fourth radial pivot junction or juncture 23. The ends of the first and second linkages 13 and 15 are pivotally connected to one another. In this manner, the linkages 13 and 15 are able to radially collapse in on themselves to a minimum radial size or dimension 200 and radially expand outwardly to a maximum radial dimension or size 300 as defined by a lock mechanism between the links 12, 14 which also provides an overextension feature (lobes with a pocket on one end thereof and a projection on the other end thereof). As best seen in FIG. 8, the curvature and pivoting of the connected links 12 and 14 of the first and second linkages 13 and 15, when collapsed, defines a "FIG. 8" or minimum radial dimension (see, e.g. FIG. 8). As best seen in FIG. 3, the curvature of the connected links 12 and 14 of the first and second linkages 11 and 13, when expanded, defines an ovoid interior 99 that defines a maximum radial dimension of the radially expandable interbody device 10. This shape approximates the end anatomy of a spinal disc (see, e.g., FIG. 9). The links 12 and 14 are joined via hinge or pivot pins 16 (see, e.g. FIG. 2) made of an appropriate biocompatible material. The hinge pins 16 may provide reference markers on the interbody device and as such would be made from a marker-distinctive material (a radio opaque material) such as tantalum. Other materials may be used.

The first link 12 is defined by a generally curved body 20 having a serrated or toothed upper surface 22 and a serrated or toothed lower surface 24. The upper and lower serrations 22 and 24 are directional (see, e.g., FIGS. 1, 2 and 3). The body 20 defines an inner curved surface 26 and an outer curved surface 28. A multi-directional threaded bore 30 is provided in the body 20. The longitudinal axis of the bore 30 is essentially perpendicular to the arc of the body 20. In order to provide connectivity at one end of the body 20 of the link 12 to another link (i.e. link 14), the body 20 has an upper hinge or flange 32 on one end thereof. The upper hinge 32 is generally rounded, defines an undersurface 34, and has an axial bore 38 extending from the upper surface 22 through the upper hinge 32 to the lower surface 24. As best seen in FIG. 2, the upper hinge 32 has a ridge or projection 36 that extends axially along the upper hinge 32. When assembled, the ridge 36 of the first link 12 co-acts with a channel, or groove or pocket 94 in the end 92 of lobes of the second link 14 to provide a lock mechanism to prevent the device from over opening or extending. The body 20 also has an end surface 40 that is below the lower surface 34 of the upper hinge 32. The end surface 40 has an axial groove, channel or pocket 42 of lobes thereof. The groove 42 co-acts with a ridge 86 of a lower hinge 84 of the second link 14 that again provides a lock mechanism to prevent the device from over opening or over extending.

In order to provide connectivity at another end of the body 20 of the link 12 to another link (i.e. link 14), the body 20 has a lower hinge or flange 44 on another end thereof. The lower hinge 44 is generally rounded, defines an upper surface 48, and has an axial bore 50 extending from the upper surface 48 through the lower hinge 44 to the lower surface 24. As best seen in FIG. 2, the lower hinge 44 has a ridge or projection 46 that extends axially along the lower hinge 44. When assembled, the ridge 46 of the lower hinge 44 of the first link 12 co-acts with a channel, groove or pocket 82 of lobes in the end 80 of the second link 14 to provide a lock mechanism to prevent the device from over opening or over extending. The body 20 also has an end surface 52 that is above the upper surface 48 of the lower hinge 44. The end surface 52 has an axial groove, channel or pocket 54 of lobes thereof. The groove 54 co-acts with a ridge 76 of an upper hinge 72 of the second link 14 that again provides a lock mechanism to prevent the device from over opening or over extending.

The second link 14 is defined by a generally curved body 60 having a serrated or toothed upper surface 62 and a serrated or toothed lower surface 64. The upper and lower serrations 62 and 64 are directional (see, e.g., FIGS. 1, 2 and 3). The body 60 defines an inner curved surface 66 and an outer curved surface 68. A multi-directional threaded bore 70 is provided in the body 60. The longitudinal axis of the bore 70 is essentially perpendicular to the arc of the body 60. In order to provide connectivity at one end of the body 60 of the link 14 to another link (i.e. link 12), the body 60 has an upper hinge or flange 72 on one end thereof. The upper hinge 72 is generally rounded, defines an undersurface 74, and has an axial bore 78 extending from the upper surface 62 through the upper hinge 72 to the lower surface 74. As best seen in FIG. 2, the upper hinge 72 has a ridge or projection 76 that extends axially along the upper hinge 72. When assembled, the ridge 76 of the second link 14 co-acts with the channel, groove or pocket 54 of lobes in the end 52 of the second link 12 to provide a lock mechanism to prevent the device from over opening or over extending. The body 60 also has an end surface 80 that is below the lower surface 74 of the upper hinge 72. The end surface 80 has an axial groove, channel or pocket 82 of lobes thereof. The groove 82 co-acts with the ridge 46 of the lower hinge 44 of the first link 12 that again provides a lock mechanism to prevent the device from over opening or over extending.

In order to provide connectivity at another end of the body 60 of the link 14 to another link (i.e. link 12), the body 60 has a lower hinge or flange 84 on another end thereof. The lower hinge 84 is generally rounded, defines an upper surface 88, and has an axial bore 90 extending from the upper surface 88 through the lower hinge 84 to the lower surface 64. As best seen in FIG. 2, the lower hinge 84 has a ridge or projection 86 that extends axially along the lower hinge 84. When assembled, the ridge 86 of the lower hinge 84 of the second link 14 co-acts with a channel, groove or pocket 42 of lobes thereof in the end 40 of the first link 12 to provide a lock mechanism to prevent the device from over opening or over extending. The body 60 also has an end surface 92 that is above the upper surface 88 of the lower hinge 84. The end surface 92 has an axial groove, channel or pocket 94 of lobes thereof. The groove 94 co-acts with the ridge 36 of the upper hinge 32 of the first link 12 that again provides a lock mechanism to prevent the device from over opening or over extending.

As depicted in FIG. 2, the links 12 and 14 are pivotally connected to one another via the hinge or pivot pins 16 that extend into the respective hinge bores of the links 12, 14. The first linkage 11 includes a first link 12 that is pivotally connected to a second link 14. Particularly, the upper hinge 32 of the first link 12 is disposed over the lower hinge 84 of the second link 14 such as to align bores 38 and 90 of the upper and lower hinges 32, 84 respectively. A pivot pin 16 is then provided in the bores 38, 90. The second linkage 13 also includes a first link 12 that is pivotally connected to a second link 14. Particularly, the upper hinge 32 of the first link 12 is disposed over the lower hinge 84 of the second link 14 such as to align bores 38 and 90 of the upper and lower hinges 32, 84 respectively. A pivot pin 16 is then provided in the bores 38, 90. As well, the first and second linkages 11, 13 are pivotally connected to one another and at both ends thereof. Particularly, the upper hinge 72 of the second link 14 of the second linkage 13 is situated over the lower hinge 44 of the first link 12 of the first linkage 11 such that the respective bores 78 and 50 are aligned. A pivot pin 16 is then provided in the bores 78, 50. The upper hinge 72 of the second link 14 of the first linkage 11 is situated over the lower hinge 44 of the first link 12 of the second linkage 13 such that the respective bores 78 and 50 are aligned. A pivot pin 16 is then provided in the bores, 78, 50. The serrations or teeth of the links are oriented to provide directional gripping during implantation and use. Particularly, the serrations of the links are oriented essentially radially when the interbody device is expanded (see, e.g., FIG. 3).

The various hinge ridges or projections of the links 12, 14 and end grooves or channels of the links 12, 14 provide various features/functions for the radially expandable interbody device 10. In one form, the hinge ridges and end groove form expansion stops for the radially expandable interbody device 10 and particularly for each link relative to other links. An expansion stop is formed by a hinge projection of one link and an end groove of another link. In the collapsed state as in FIG. 8, the links 12, 14 of the interbody device 10 are oriented such that hinge projections of one link and adjacent end grooves of an adjacent link do not register and thus are free to pivot relative to one another. When the radially expandable interbody device 10 is expanded (see, e.g., FIG. 9), the links 12, 14 pivot such that the hinge projections of one link and adjacent end grooves of an adjacent link do register thus providing a pivot locking mechanism at a maximum expansion of the links. This provides over extension prevention.

The version of the interbody device as shown in the figures has four (4) segments or links that form the body thereof. It should be appreciated, however, that the interbody device may be fashioned from additional or more than four segments or links. Thus, the interbody device may be formed of a body having up to n segments or links.

Figure 7:
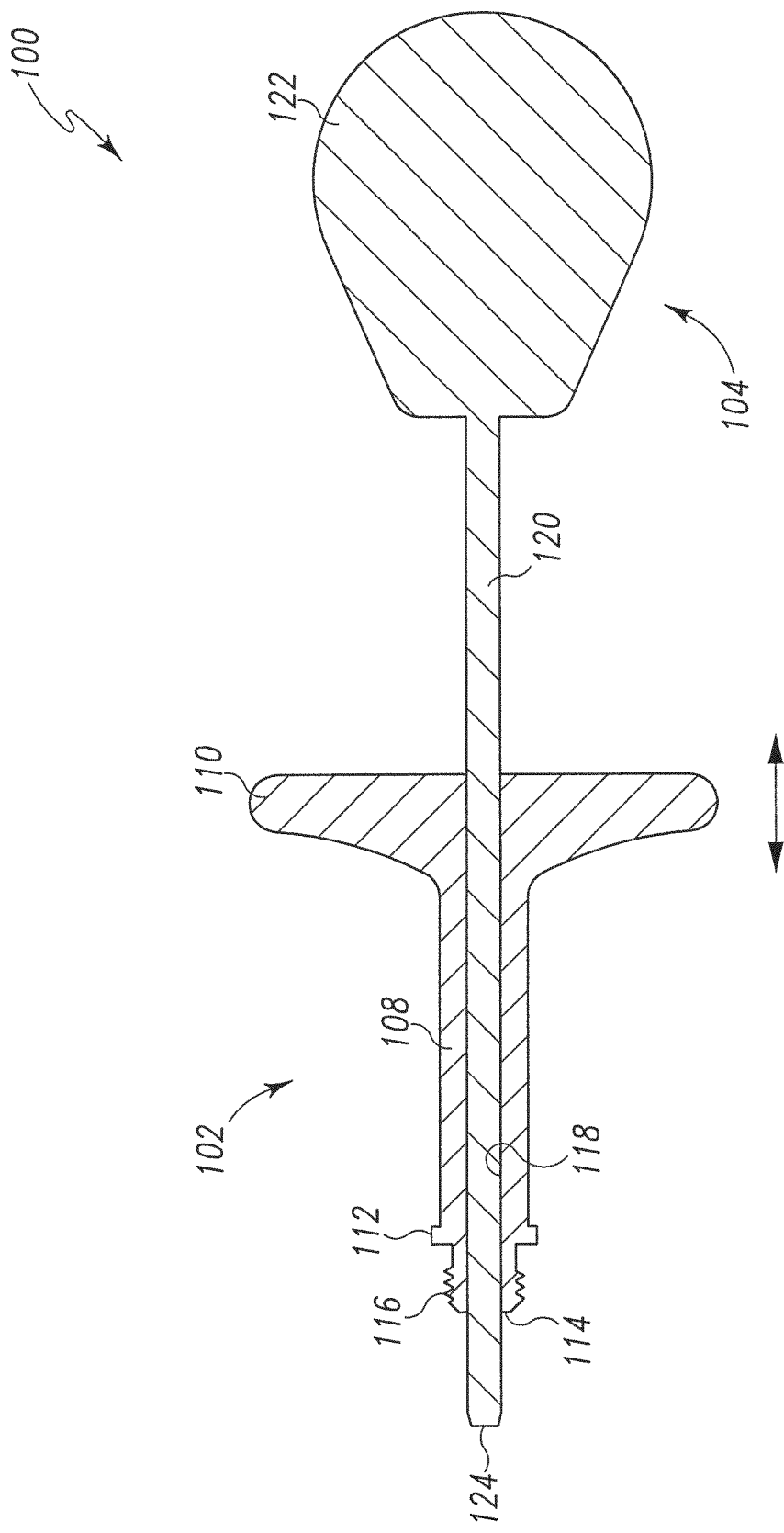
FIG. 7 is a sectional view of an implantation and deployment device for use with the radially expandable spinal interbody device of FIG. 1.

FIG. 7 depicts a surgical tool 100 that may be used with and/or for the implantation and deployment of the radially expandable interbody device 10. Particularly, the surgical tool 100 is used for various implantation functions such as reaming of an implant site, deploying the radially expandable interbody device 10, and the insertion of bone graft, allograft or BMP within the radially expandable interbody device 10. The surgical tool 100 is fashioned from an appropriate bio-compatible material such as one or more of those described above. The surgical tool 100 includes a positioning portion 102 and a deploy portion 104. The positioning portion 102 is defined by a cylindrical body or shaft 108 having a handle 110 formed at one end of the shaft 108 and a tapered end 114 formed at another end of the shaft 108 distal the handle 110. External threads 116 are formed on the end 114. These threads are sized to correspond to the threaded bores 30 and 70 of the links 12 and 14 respectively of the interbody device 10. In this manner, the positioning tool 102 may be threadedly coupled to the interbody device 10 during implantation and orientation. (see, e.g. FIGS. 8 and 9). The shaft 108 has a bore 118 that extends from the end 114 to and through the handle 110.

The deploy portion 104 is defined by a rod 120 extending from a grip 122. The rod 120 is dimensioned to be received in the shaft bore 118 and extend axially therefrom. The rod 120 has a tapered end 124 at an end of the rod 120 distal the grip 122. The grip 122 forms a handle that is essentially bulb-shaped. The deploy portion 104 is thus configured to axially move back and forth relative to the positioning portion 102. When the positioning tool 102 is attached to the radially expandable interbody device 10 and the interbody device 10 has been appropriately placed at an implant site (see, e.g., FIGS. 8 and 9), axial movement of the deploy portion 104 expands the radially expandable interbody device 10 as shown in an unexpanded state in FIG. 8, to the expanded radially expandable interbody device 10 as shown in an expanded state in FIG. 9.

Figure 4:
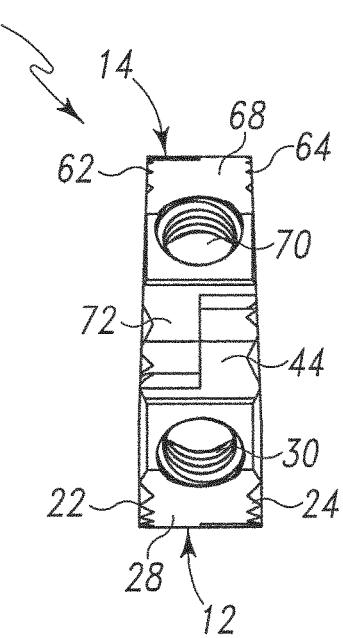
FIG. 4 is a side view of the radially expandable spinal interbody device of FIG. 3 taken along ling 4-4 thereof.
Figure 5:
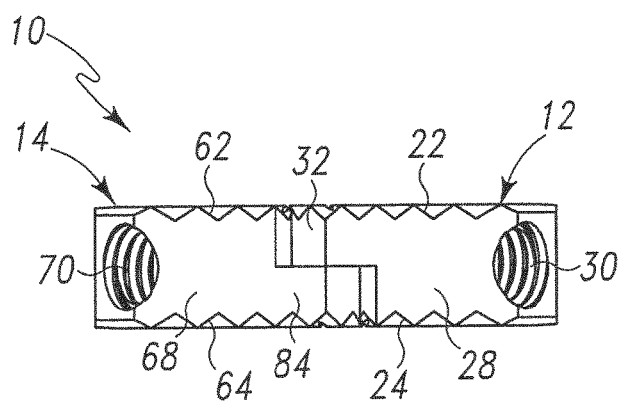
FIG. 5 is a side view of the radially expandable spinal interbody device of FIG. 3 taken along line 5-5 thereof.
Figure 6:
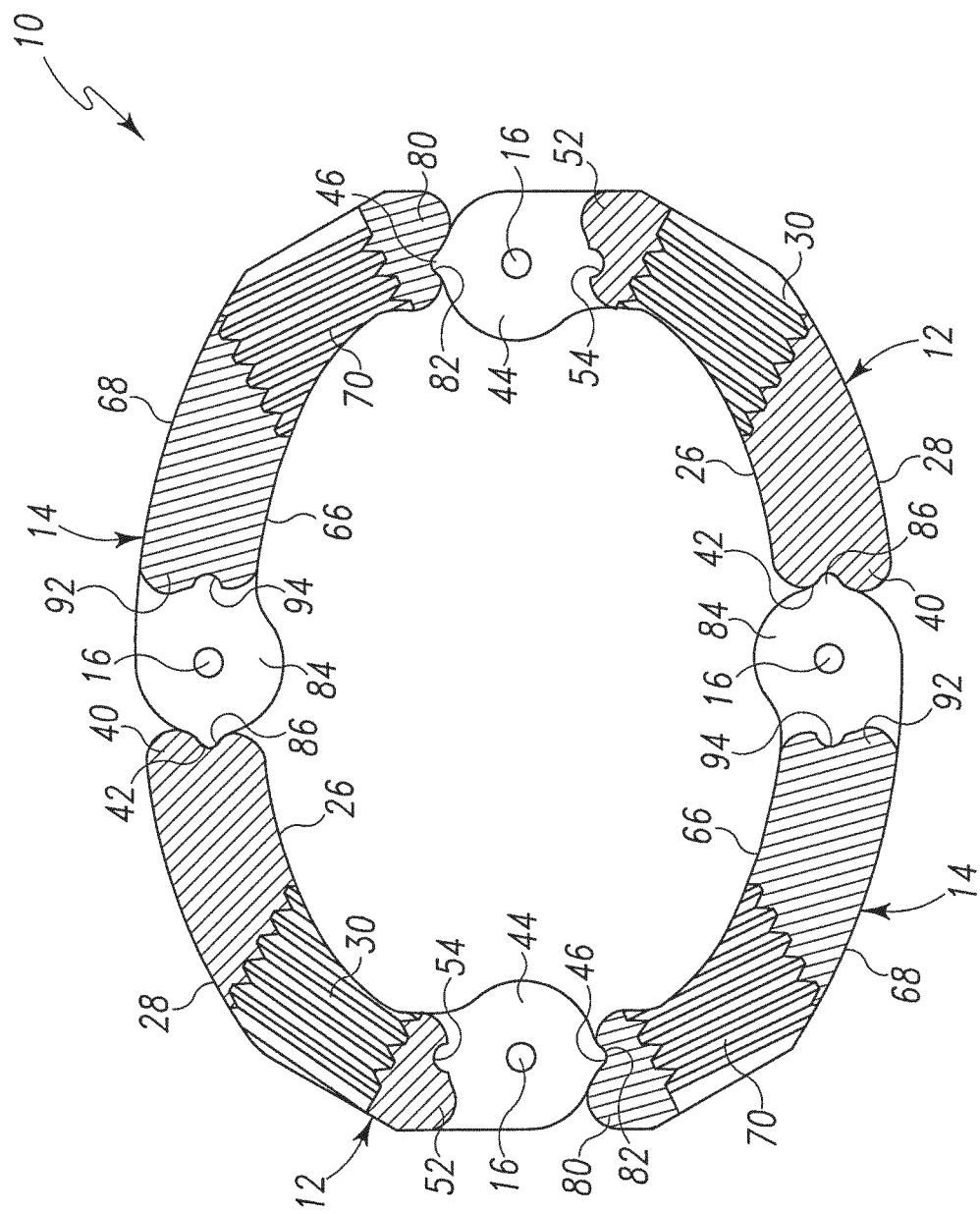
FIG. 6 is a sectional view of the radially expandable spinal interbody device of FIG. 1 taken along line 6-6 thereof.

Referring now to FIGS. 10-18, a spinal interbody device 210 is shown according to an exemplary embodiment. Device 210 includes a first link 212, a second link 214, and a third or base link 216. First link 212 is pivotally connected to second and third links 214, 216 via pivot pins 218, 220. Similarly, second link 214 is pivotally connected to third link 216 via a pivot pin 222. Pivot pins 218, 220, 222 form hinge mechanisms acting between links 212, 214, and 216 such that device 210 can be moved from a first, radially collapsed, or retracted configuration, as shown in FIG. 2, to a second, or radially expanded configuration, as shown in FIG. 4. Similar to device 10, device 210 is implantable between adjacent vertebrae in a radially collapsed configuration and, once in proper position, is expandable through and up to a maximum radially expanded position. Device 210 may share many features of device 10, and all such combinations of features are understood to be within the scope of the present disclosure.

According to an exemplary embodiment, first link 212 includes a first end 224 and a second end 226. Upper and lower surfaces 228, 230 and inner and outer surfaces 232, 234 extend between first end 224 and second end 226. Upper and lower surfaces 228, 230 include serrations 236 (e.g., grooves, teeth, projections, etc.) that may extend along all or a portion of the length of first link 212 between first end 224 and second end 226. Inner surface 232 may be curved such that when device 210 is expanded, links 212, 214, 216 form a generally oval-shaped interior. First and second ends 224, 226 include projections 238, each projection 238 having an aperture 240 extending therethrough that is configured to receive one of pivot pins 218, 220.

Second link 214 includes a first end 244 and a second end 246. Upper and lower surfaces 248, 250 and inner and outer surfaces 252, 254 extend between first end 244 and second end 246. Upper and lower surfaces 248, 250 include serrations 256 (e.g., grooves, teeth, projections, etc.) that may extend along all or a portion of the length of second link 214 between first end 244 and second end 246. Inner surface 252 may be curved such that when device 210 is expanded, links 212, 214, 216 form a generally oval-shaped interior. First end 244 of second link 214 includes a channel or recess 258 that is configured to receive projection 238 of first link 212. First end 244 also includes an aperture 264 extending therethrough that is configured to receive pivot pin 220. Second end 246 of second link 214 includes a projection 260 having an aperture 264 extending therethrough that is configured to receive pivot pin 222.

Third link 116 includes a body 268 having a first end 270 and a second end 272. Upper and lower surfaces 274, 276 and inner and outer surfaces 278, 280 extend between first end 270 and second end 272. First end 270 includes a rounded, narrowed end portion 184 (e.g., a bull nose portion, etc.) that may narrow between upper and lower surfaces 274, 276 and/or between inner and outer surfaces 278, 280, and facilitate insertion of device 210 into a desired area within a patient. Upper and lower surfaces 274, 276 include serrations 282 (e.g., grooves, teeth, projections, etc.) that may extend along all or a portion of the length of third link 216 between first end 270 and second end 272. Inner surface 278 may be curved such that when device 210 is expanded, links 212, 214, 216 form a generally oval-shaped interior.

Figure 17:
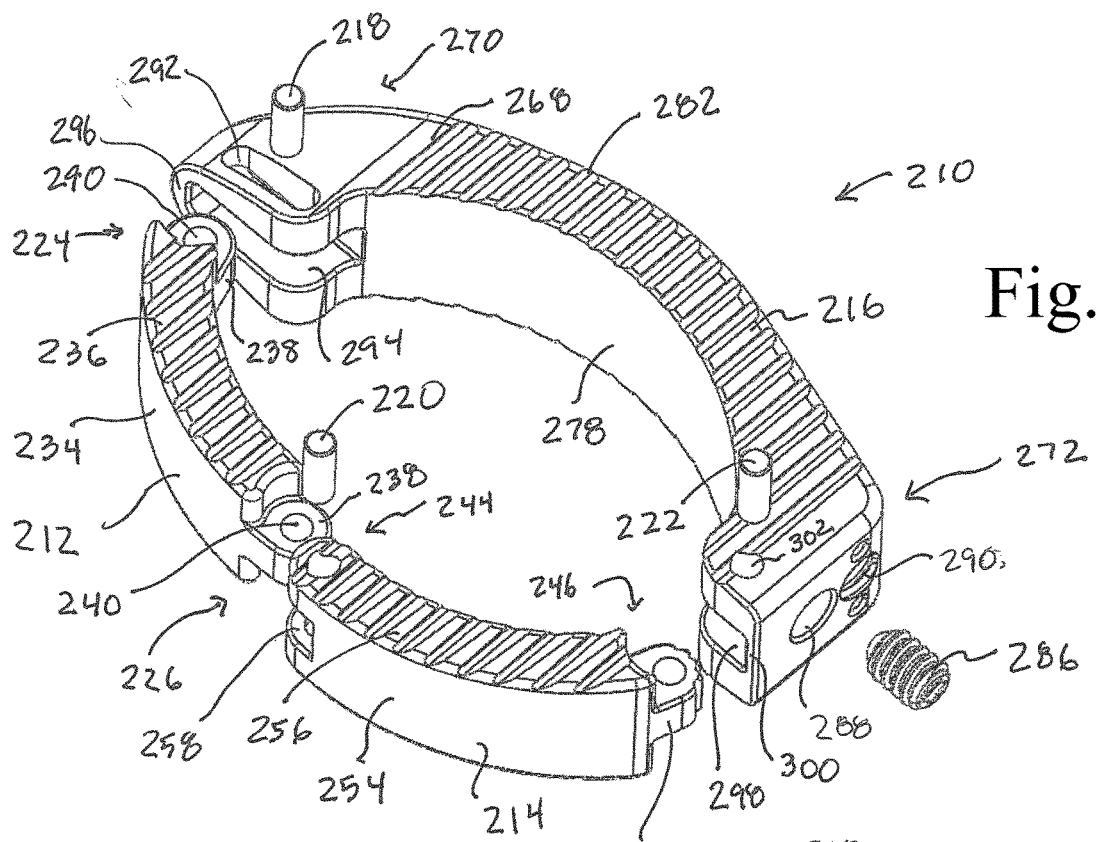
FIGS. 17-18 are exploded perspective views of the device of FIG. 10 according to exemplary embodiments.

First end 270 of third link 216 includes a slot 292 (e.g., an elongated aperture, recess, etc.) that is configured to receive pivot pin 218 and enable pivot pin 218 to pivot and translate within slot 292. As such, first link 212 is able to move in both a pivoting and translating manner. An end wall 296 limits the pivoting and translational movement of first link 212 relative to third link 216 as device 210 is moved between a radially collapsed position and a radially expanded position. First end 270 further includes a channel, groove, or recess 294 that is configured to receive projection 238 (e.g., lobe, knuckle, hinge portion or member, etc.) on first link 212. As shown in FIG. 17, pivot pin 218 is received within slot 292 in third link 216 and aperture 240 in first link 212.

Figure 18:
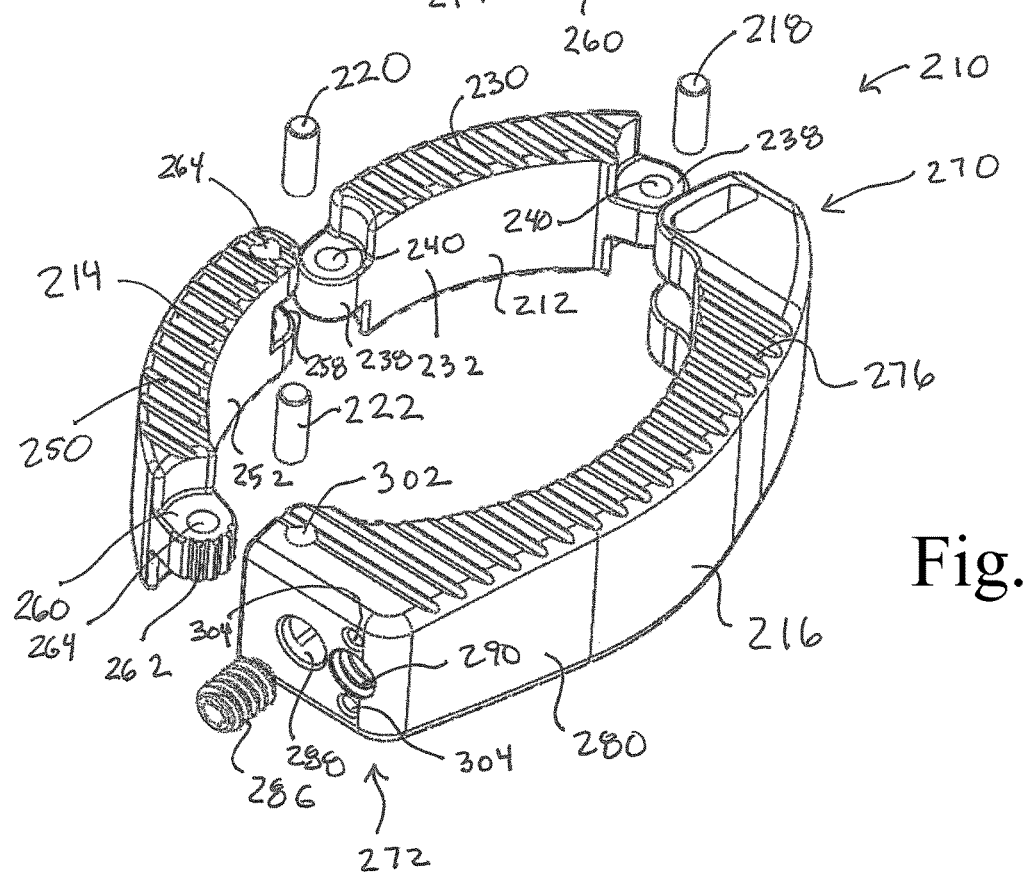

Second end 272 of third link 216 includes a channel or recess 298 configured to receive projection 260 on second link 214. As shown in FIG. 18, pivot pin 222 is received within aperture 302 in third link 216 and aperture 264 in second link 214. As such, link 214 is configured to move relative to third link 216 in only a rotating or pivoting manner (and, unlike first link 212, not in a translating manner) as device 210 moves between a radially collapsed position and a radially expanded position.

Second end 272 of third link 216 further includes a screw, or worm, 286 that is received within a bore 288 in second end 272. Worm 286 is configured to engage gears 262 (e.g., teeth, etc.) on projection 260 of second link 214 such that rotation of worm 286 about its longitudinal axis (e.g., by way of a tool, etc.) causes a corresponding rotation of second link 214 about pivot pin 222. In this manner the radially collapsing and expanding movement of device 210 can be controlled via rotation of worm 286, which together with projection 260 and gears 262, forms a worm drive enabling adjustable control of the expansion of device 210. Worm 286 may include a suitable recess (e.g., a hex recess, etc.) that enables rotation of worm 286 by any suitable tool (e.g., a screwdriver, etc.). On either side of aperture 290 are a pair of recesses 304. Recesses 304 may be configured to receive a portion of the insertion tool and prevent rotation of device 210 relative to the tool, thereby enabling a user to manipulate device 210 (e.g., rotate, adjust, etc.).

Figure 14:
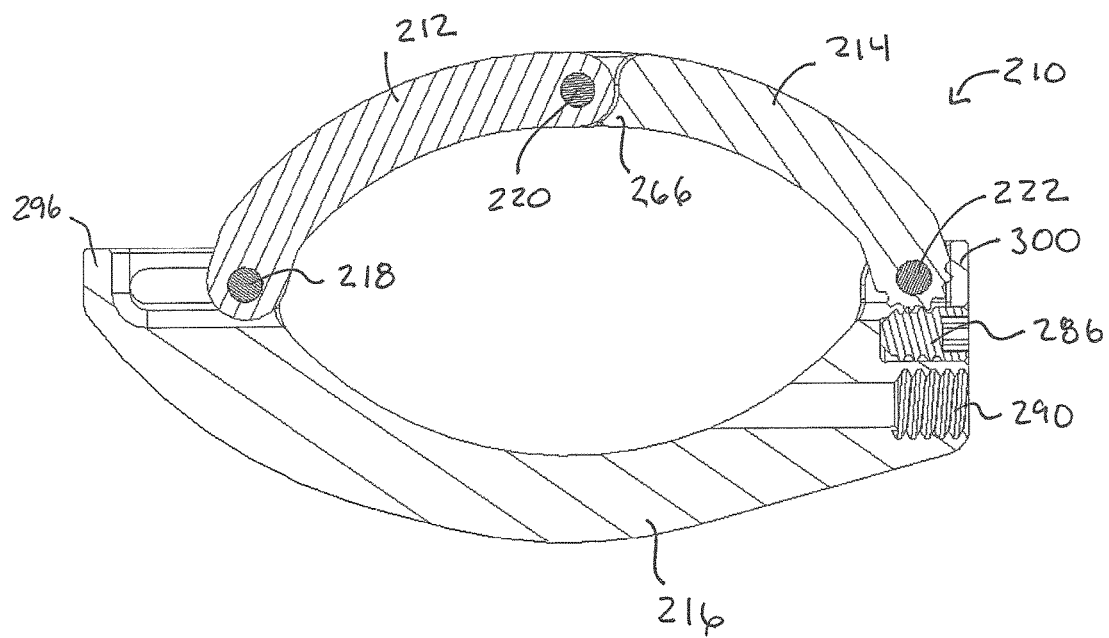
FIG. 14 is a cross-sectional view of the device of FIG. 13 according to an exemplary embodiment.

According to an exemplary embodiment, second end 272 of third link 216 further includes an aperture 290. As shown in FIG. 14, aperture 290 may extend through third link 216, and all or a portion of the length of aperture 290 may be threaded. In some embodiments, aperture 290 is configured to threadingly receive a tool (e.g., an insertion tool, etc.) that may be inserted into aperture 290, used to properly position device 210 within a patient, and subsequently removed from device 210. Aperture 290 may further enable the insertion of bone growth or similar materials into the cavity formed by device 210. Any suitable tool, including tools similar to those disclosed elsewhere herein, may be used in combination with device 210.

Figure 13:
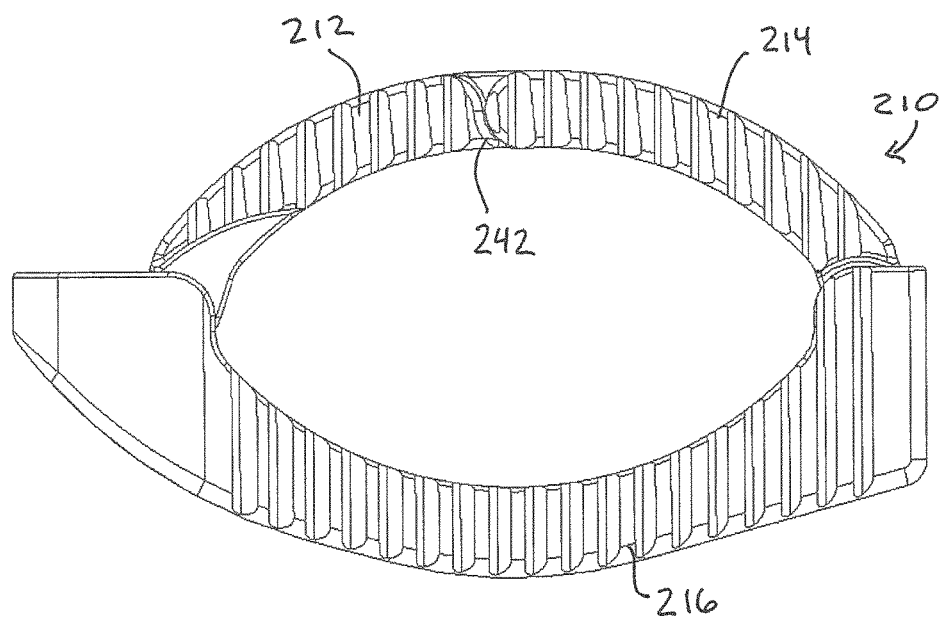
FIG. 13 is a top view of the device of FIG. 10 is a radially expanded configuration according to an exemplary embodiment.
Figure 15:
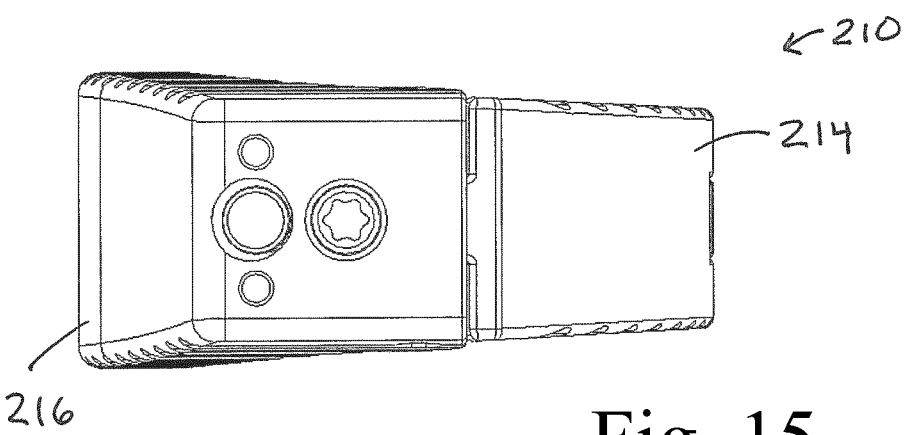
FIG. 15 is a side view of the device of FIG. 10 in a radially expanded configuration according to an exemplary embodiment.
Figure 16:
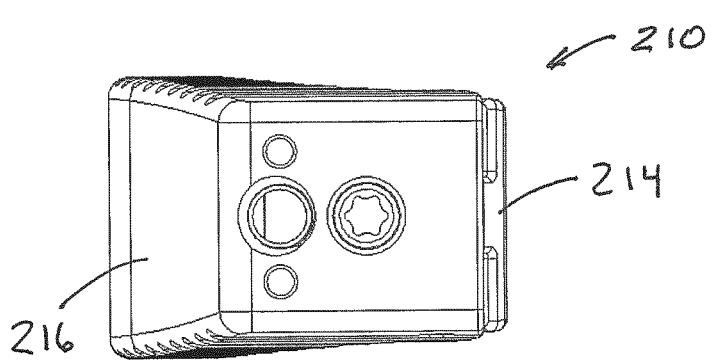
FIG. 16 is a side view of the device of FIG. 10 in a radially collapsed configuration according to an exemplary embodiment.

In use, device 210 may initially be in a radially collapsed configuration, as shown, for example, in FIGS. 10-12 and 16. In the collapsed configuration, pivot pin 220 and the hinge mechanism coupling first link 212 to second link 214 may be adjacent third link 216. Device 210 may be inserted into a patient in a desired position using a suitable insertion tool. Once in a desired position, device 210 may be radially expanded to an expanded configuration, as shown in FIGS. 13-15. To expand/collapse device 210, a tool may be inserted into worm 286 and rotated, such that rotation of worm 286 causes rotation of second link 214 toward an expanded position. First link 212, by way of its pivotal linkage to second link 214, is in turn also moved to an expanded position. In an expanded position, pivot pin 220 and the hinge mechanism coupling first link 212 to second link 214 may extend away from third link 216.

According to one embodiment, first link 212, second link 214, and/or third link 216 include motion limiting features intended to limit the range of motion of the links relative to one another. For example, referring to FIG. 14, device 210 is shown in a radially expanded configuration. First link 212 includes a lip 242 that may be provided on one or both of upper and lower surfaces 228, 230 of first link 212 and that acts to engage second link 214 to limit the relative range of motion between the links. Similarly, second link 214 includes a lip 266 that engages first link 212 to likewise limit the relative range of motion between the links. Third link 216 includes end walls 296, 300 that limit the relative range of motion of first link 212 (both pivotally and translationally) and second link 214 (only pivotally). According to various alternative embodiments, other features may be provided to further define and/or limit the range of motion of links 212, 214, and 216.

It should be noted that while the FIGURES generally illustrate device 210 in either a fully radially collapsed position or a fully radially expanded position, according to various alternative embodiments, device 210 is configured to be implanted in any intermediate position between the fully collapsed configuration and the fully expanded configuration. Furthermore, in some embodiments, the worm drive components may be omitted such that device 210 is moved between a fully collapsed configuration and a fully expanded configuration in a similar manner to device 10.

Figure 21:
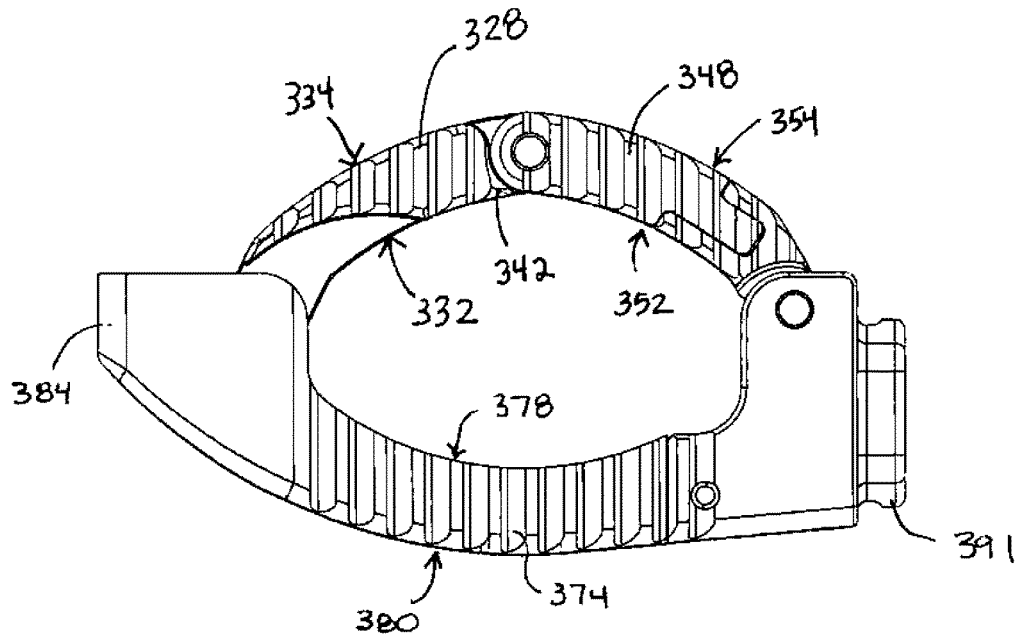
FIG. 21 is a top view of the device of FIG. 19 according to one embodiment.

Referring now to FIGS. 19-25, a spinal interbody device 310 is shown according to an exemplary embodiment. As shown in FIGS. 19-22, device 310 includes a first link 312, a second link 314, and a third or base link 316. First link 312 is pivotally connected to second and third links 314, 316 via pivot pins 318, 320. Similarly, second link 314 is pivotally connected to third link 316 via a pivot pin 322. Pivot pins 318, 320, 322 form hinge mechanisms acting between links 312, 314, and 316 such that device 310 can be moved from a first, radially collapsed, or retracted configuration, (similar to that shown in FIG. 2), to a second, or radially expanded configuration, as shown in FIG. 21. Similar to devices 10 and 210, device 310 is implantable between adjacent vertebrae in a radially collapsed configuration and, once in proper position, is expandable through and up to a maximum radially expanded position. Device 310 may share many features of device 10 and/or device 210, and all such combinations of features are understood to be within the scope of the present disclosure.

Figure 22:
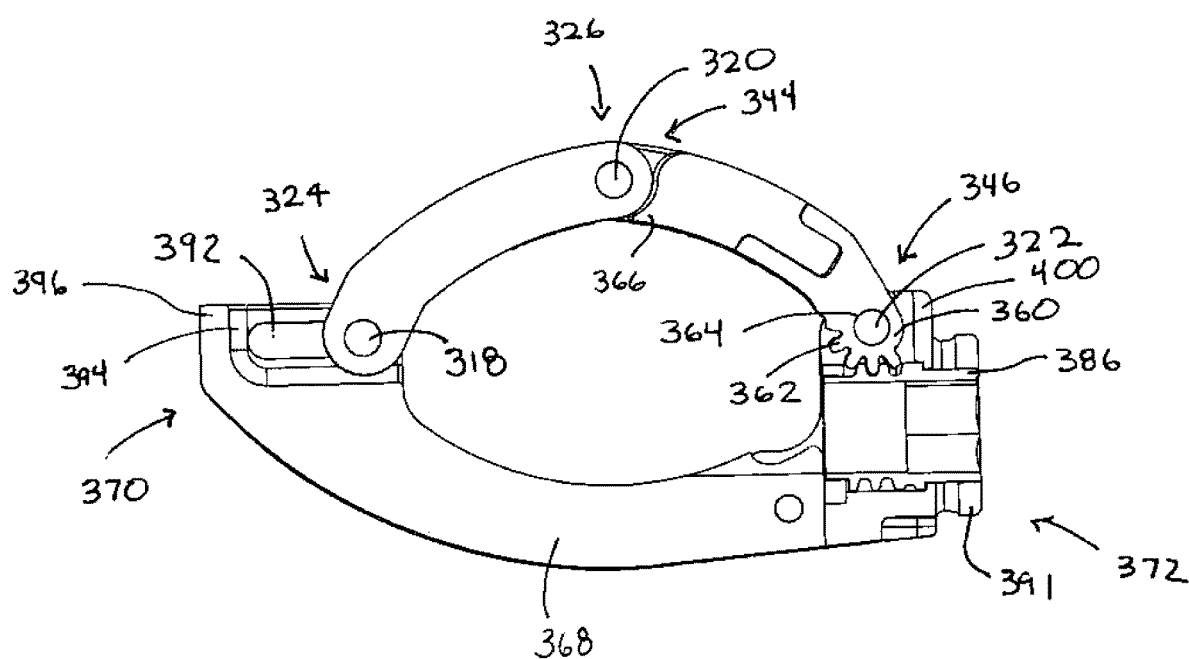
FIG. 22 is a cross-sectional view of the device of FIG. 19 according to one embodiment.
Figure 23:
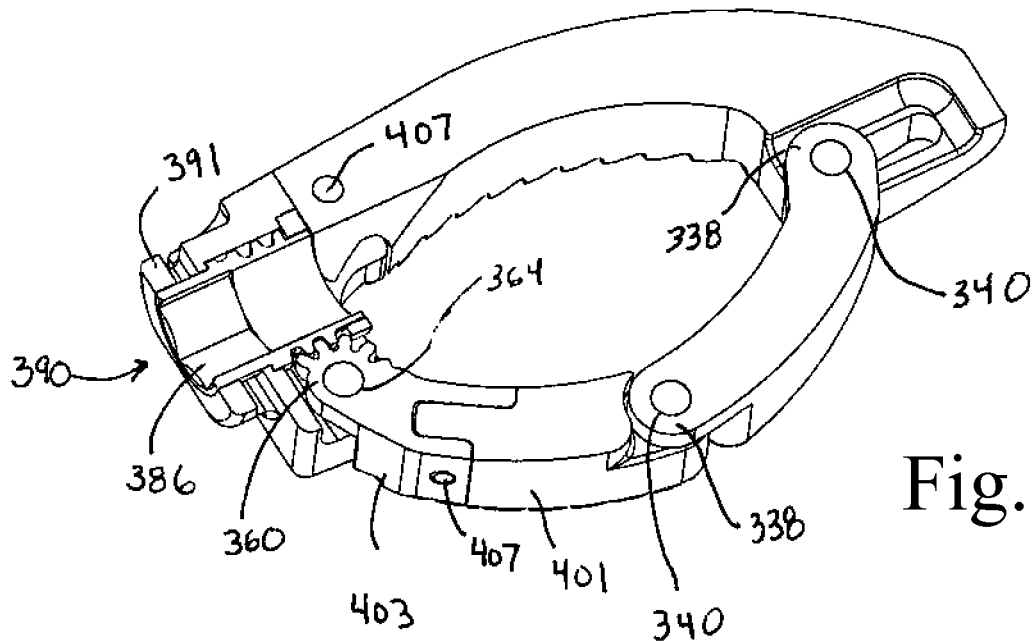
FIG. 23 is a cross-sectional perspective view of the device of FIG. 19 according to one embodiment.
Figure 24:
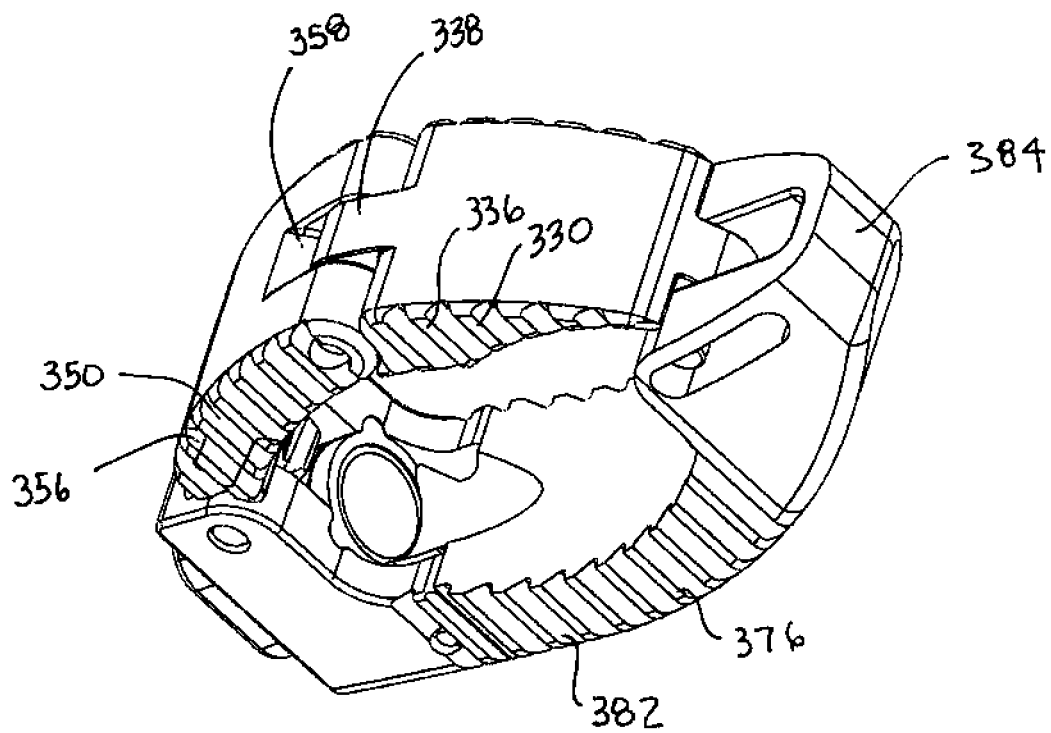
FIG. 24 is another perspective view of the device of FIG. 19 according to one embodiment.
Figure 25:
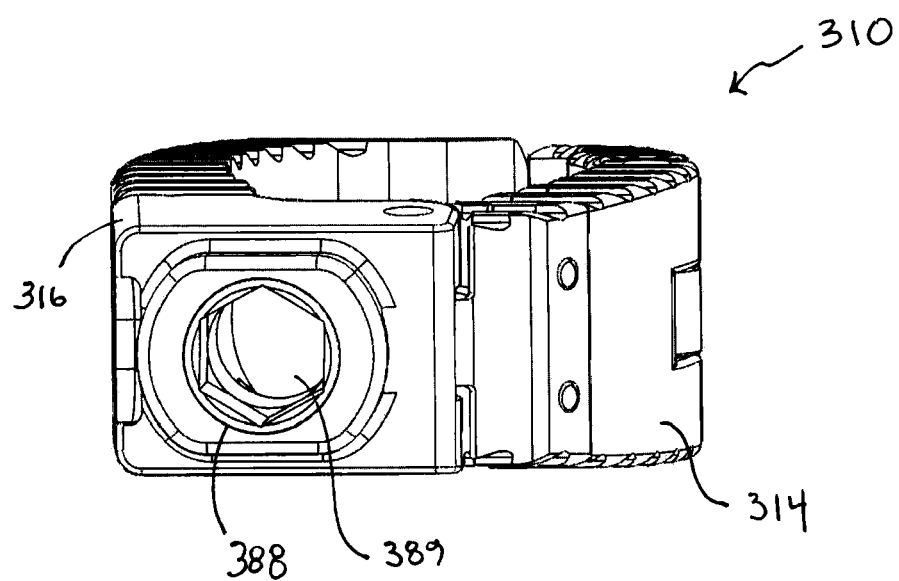
FIG. 25 is a side view of the device of FIG. 19 according to one embodiment.

Referring to FIGS. 22-24, according to an exemplary embodiment, first link 312 includes a first end 324 and a second end 326. Upper and lower surfaces 328, 330 and inner and outer surfaces 332, 334 extend between first end 324 and second end 326. Upper and lower surfaces 328, 330 include serrations 336 (e.g., grooves, teeth, projections, etc.) that may extend along all or a portion of the length of first link 312 between first end 324 and second end 326. Inner surface 332 may be curved such that when device 310 is expanded, links 312, 314, 316 form a generally oval-shaped interior. First and second ends 324, 326 include projections 338, each projection 338 having an aperture 340 extending therethrough that is configured to receive one of pivot pins 318, 320.

Second link 314 includes a first end 344 and a second end 346. Upper and lower surfaces 348, 350 and inner and outer surfaces 352, 354 extend between first end 344 and second end 346. Upper and lower surfaces 348, 350 include serrations 356 (e.g., grooves, teeth, projections, etc.) that may extend along all or a portion of the length of second link 314 between first end 344 and second end 346. Inner surface 352 may be curved such that when device 310 is expanded, links 312, 314, 316 form a generally oval-shaped interior. First end 344 of second link 314 includes a channel or recess 358 that is configured to receive projection 338 of first link 312. First end 344 also includes an aperture 364 extending therethrough that is configured to receive pivot pin 320. Second end 346 of second link 314 includes a projection 360 having an aperture 364 extending therethrough that is configured to receive pivot pin 322.

Third link 116 includes a body 368 having a first end 370 and a second end 372. Upper and lower surfaces 374, 376 and inner and outer surfaces 378, 380 extend between first end 370 and second end 372. First end 370 includes a rounded, narrowed end portion 384 (e.g., a bull nose portion, etc.) that may narrow between upper and lower surfaces 374, 376 and/or between inner and outer surfaces 378, 380, and facilitate insertion of device 310 into a desired area within a patient. Upper and lower surfaces 374, 376 include serrations 382 (e.g., grooves, teeth, projections, etc.) that may extend along all or a portion of the length of third link 316 between first end 370 and second end 372. Inner surface 378 may be curved such that when device 310 is expanded, links 312, 314, 316 form a generally oval-shaped interior.

First end 370 of third link 316 includes a slot 392 (e.g., an elongated aperture, recess, etc.) that is configured to receive pivot pin 318 and enable pivot pin 318 to pivot and translate within slot 392. As such, first link 312 is able to move in both a pivoting and translating manner. An end wall 396 limits the pivoting and translational movement of first link 312 relative to third link 316 as device 310 is moved between a radially collapsed position and a radially expanded position. First end 370 further includes a channel, groove, or recess 394 that is configured to receive projection 338 (e.g., lobe, knuckle, hinge portion or member, etc.) on first link 312. As shown in FIG. 23, pivot pin 318 is received within slot 392 in third link 316 and aperture 340 in first link 312.

Second end 372 of third link 316 includes a channel or recess 398 configured to receive projection 360 on second link 314. As shown in FIG. 23, pivot pin 322 is received within aperture 302 in third link 316 and aperture 364 in second link 314. As such, second link 314 is configured to move relative to third link 316 in only a rotating or pivoting manner (and, unlike first link 312, not in a translating manner) as device 310 moves between a radially collapsed position and a radially expanded position.

Second end 372 of third link 316 further includes a screw, or worm, 386 that is received within a bore 388 in second end 372. Worm 386 is configured to engage gears 362 (e.g., teeth, etc.) on projection 360 of second link 314 such that rotation of worm 386 about its longitudinal axis (e.g., by way of a tool, etc.) causes a corresponding rotation of second link 314 about pivot pin 322. In this manner the radially collapsing and expanding movement of device 310 can be controlled via rotation of worm 386, which together with projection 360 and gears 362, forms a worm drive enabling adjustable control of the expansion of device 310. Worm 386 may include a suitable recess 389 (e.g., a hex recess, etc.) that enables rotation of worm 386 by any suitable tool (e.g., a screwdriver, etc.).

According to an exemplary embodiment, worm 386 defines an aperture 390 (e.g., a central aperture, etc.). As shown in FIG. 23, aperture 390 may extend through third link 316. In some embodiments, aperture 390 is configured to receive a tool (e.g., an insertion tool, etc.) that may be inserted into aperture 390, used to properly position device 310 within a patient, and subsequently removed from device 310. Aperture 390 may further enable the insertion of bone growth or similar materials into the cavity formed by device 310. Any suitable tool, including tools similar to those disclosed elsewhere herein, may be used in combination with device 310. In one embodiment, a portion of aperture 190 is hex shaped to receive a correspondingly-shaped tool.

In some embodiments, second end 372 may include a boss, or raised portion 391. One or more recesses 393, 395 may be provided on one or both sides of raised portion 391 to enable grasping of device 310 by a suitable tool. In one embodiment, recesses 393 are provided on opposing sides of boss 391 and provide undercut areas usable to retain an end of a tool.

Figure 19:
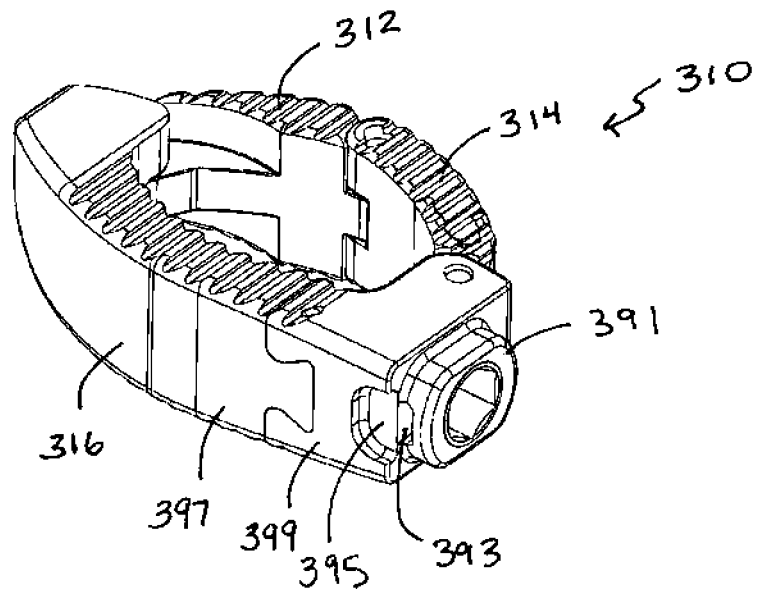
FIGS. 19-20 are perspective views of a spinal interbody device according to another embodiment.
Figure 20:
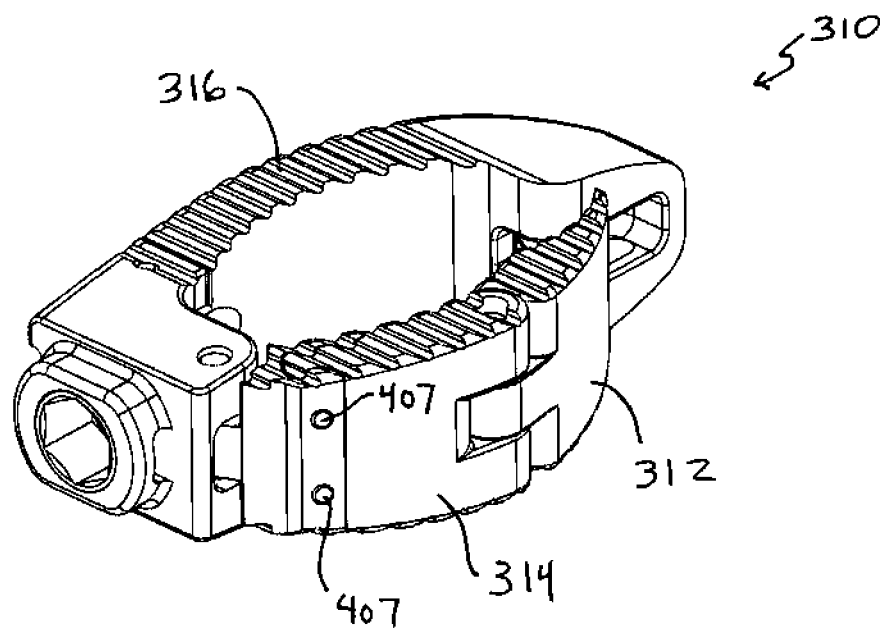

Referring now to FIGS. 19 and 22, while in some embodiments one or more of links 312, 314, 316 may be made of a single material (e.g., PEEK, etc.), in other embodiments, multiple materials may be used to form discreet portions of one or more of links 312, 314, 316.

For example, as shown in FIG. 19, in one embodiment, third link 316 may include a first portion 397 and a second portion 399. In one embodiment portions 397 and 399 are different materials. For example, first portion 397 may be a polymer (e.g., PEEK) and second portion 399 may be a metal (e.g., titanium, etc.). First portion 397 and second portion 399 may be divided by a dovetail configuration or other separating geometry. In some embodiments, first portion 397 is molded over second portion 399. In other embodiments, other ways of joining first and second portions 397, 399 may be used.

Similarly, as shown in FIG. 22, in one embodiment, second link 314 may include a first portion 401 and a second portion 403. In one embodiment portions 401 and 403 are different materials. For example, first portion 401 may be a polymer (e.g., PEEK) and second portion 403 may be a metal (e.g., titanium, etc.). First portion 401 and second portion 403 may be divided by a curved configuration (e.g., U-shaped, etc.) or other separating geometry. In some embodiments, first portion 397 is molded over second portion 399. In other embodiments, other ways of joining first and second portions 397, 399 may be used.

Using differing materials for first and second portions may provide added strength where needed, such as with second portion 399 (to retain worm 386) and second portion 403 (to interact with worm 386). The first and second portions 397, 399 and 401, 403 may be joined together using any suitable methods, including overmolding, mechanical fasteners, and the like. In one embodiment, pins 407 are used to maintain the first and second portions in position In use, device 310 may initially be in a radially collapsed configuration, as shown, for example, in FIGS. 10-12 and 16 with respect to device 210. In the collapsed configuration, pivot pin 320 and the hinge mechanism coupling first link 312 to second link 314 may be adjacent third link 316. Device 310 may be inserted into a patient in a desired position using a suitable insertion tool. Once in a desired position, device 310 may be radially expanded to an expanded configuration, as shown in FIGS. 21-23. To expand/collapse device 310, a tool may be inserted into worm 386 and rotated, such that rotation of worm 386 causes rotation of second link 314 toward an expanded position. First link 312, by way of its pivotal linkage to second link 314, is in turn also moved to an expanded position. In an expanded position, pivot pin 320 and the hinge mechanism coupling first link 312 to second link 314 may extend away from third link 316.

According to one embodiment, first link 312, second link 314, and/or third link 316 include motion limiting features intended to limit the range of motion of the links relative to one another. For example, referring to FIG. 21, device 310 is shown in a radially expanded configuration. First link 312 includes a lip 342 that may be provided on one or both of upper and lower surfaces 328, 330 of first link 312 and that acts to engage second link 314 to limit the relative range of motion between the links. Similarly, second link 314 includes a lip 366 that engages first link 312 to likewise limit the relative range of motion between the links. Third link 316 includes end walls 396, 400 that limit the relative range of motion of first link 312 (both pivotally and translationally) and second link 314 (only pivotally). According to various alternative embodiments, other features may be provided to further define and/or limit the range of motion of links 312, 314, and 316.

It should be noted that while the FIGURES generally illustrate device 310 in a fully radially expanded position, according to various alternative embodiments, device 310 is configured to be implanted in any intermediate position between the fully collapsed configuration and the fully expanded configuration. Furthermore, in some embodiments, the worm drive components may be omitted such that device 310 is moved between a fully collapsed configuration and a fully expanded configuration in a similar manner to device 10. Further yet, while some embodiments illustrate certain components as including both metal and polymer portions, in various alternative embodiments any components may be made of a single material (e.g., a bio-compatible material such as PEEK, titanium, etc.).

Figure 26:
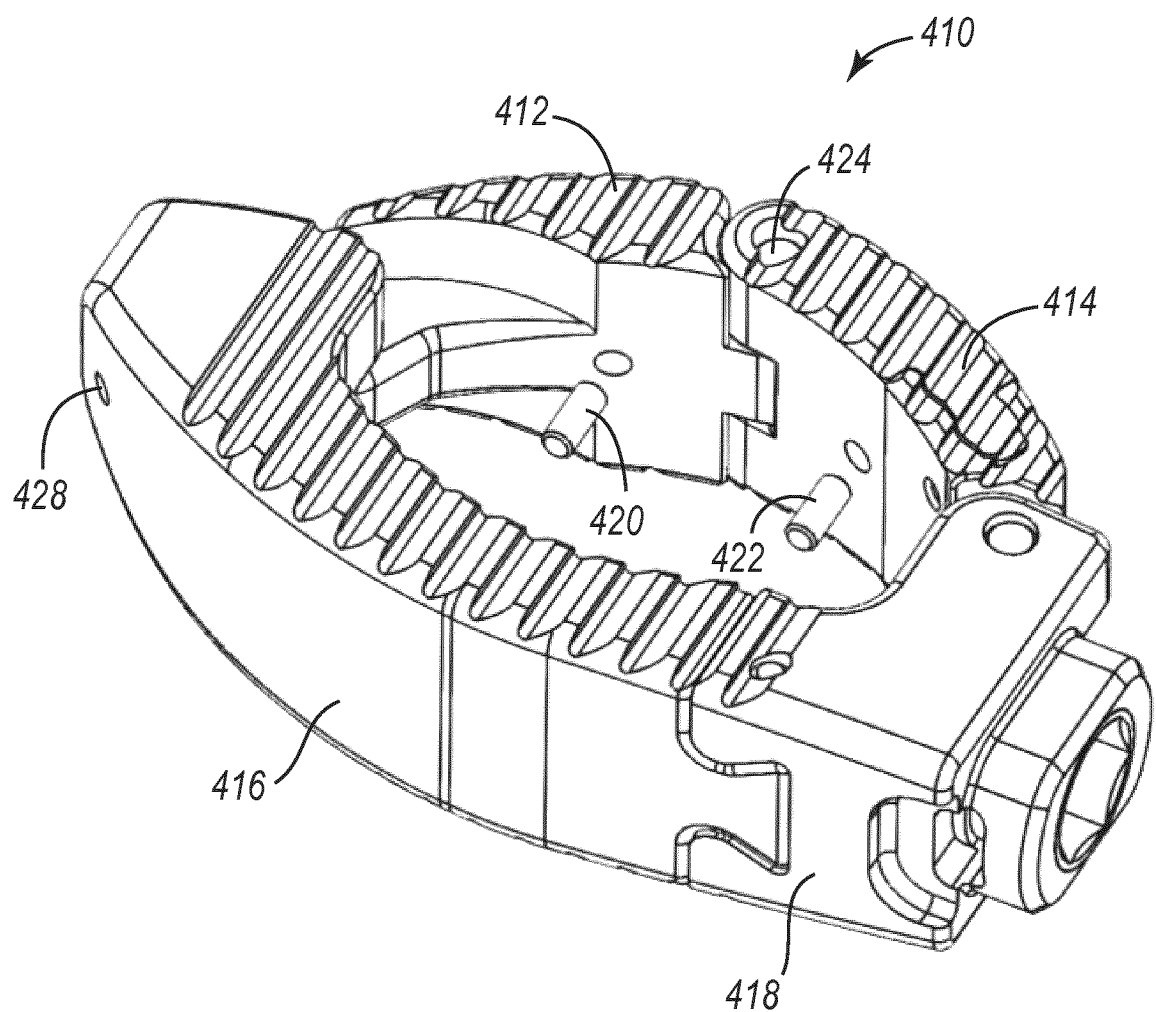
FIG. 26 is a perspective view of a spinal interbody device according to another embodiment.

Referring now to FIGS. 26-33, a spinal interbody device 410 is shown according to an exemplary embodiment. As shown in FIG. 26, device 410 includes a first link 412, a second link 414, and a third or base link 416. Third link 416 includes adjustment portion 418, which includes adjustment features to facilitate expansion/contraction of device 410. Device 410 can be moved from a first, radially collapsed, or retracted configuration, (similar to that shown in FIG. 27), to a second, or radially expanded configuration (similar to that shown in FIG. 26). Similar to devices 10, 210, and 310, device 410 is implantable between adjacent vertebrae in a radially collapsed configuration and, once in proper position, is expandable through and up to a maximum radially expanded position. Device 410 is substantially the same as device 310, with the exception of the imaging components and placement thereof discussed in greater detail below, and as such may share many features of device 310. All such combinations of features are understood to be within the scope of the present disclosure.

In one embodiment, device 410 includes one or more imaging elements (e.g., elements configured to be viewable with an imaging device such as an x-ray, etc.) configured to facilitate insertion and adjustment of device 410. For example, referring to FIGS. 26-32, device 410 includes adjustment end 418, gauge elements or pins 420, 422, pivot pins 424, 426, and locator element or pin 428, any or all of which may be provided as imaging elements.

In one embodiment, an imaging element is a radiopaque element configured to be opaque to x-rays. In some embodiments, the non-imaging elements of device 410 are radiolucent. As such, when using an x-ray during insertion of device 410, components 418, 420, 422, 424, 426, and 428 will be visible on the x-ray image device (see, e.g., FIGS. 29 and 32) in the form of image portions. One or more imaging elements may be configured to provide an indication or gauge (e.g., a visual indication or gauge) of a degree of expansion of device 410 when imaged from a predetermined imaging perspective.

In one embodiment gauge pins or elements 420, 422 are elongated and cylindrical in shape. In other embodiments, other shapes may be used. Gauge pins 420, 422 are fixed in place within correspondingly shaped bores in first and second links 412, 414. In other embodiments, gauge pins 420, 422 may be located in other suitable locations. Gauge pins 420, 422 are positioned in device 410 such that as device 410 is expanded or collapsed, an image portion (e.g., an x-ray image) generated from a predetermined perspective relative to device 410 changes in shape. In some embodiments, a length of the image portion changes as device 410 is expanded/contracted, thereby providing a visual indication of the degree of expansion of device 410. For example, in some embodiments, an image portion based on gauge pins 420, 422 initially resembles a "dash" (see FIG. 29), and as the device is expanded, the length of the dash decreases until the image portion resembles a circle (see FIG. 32).

Figure 27:
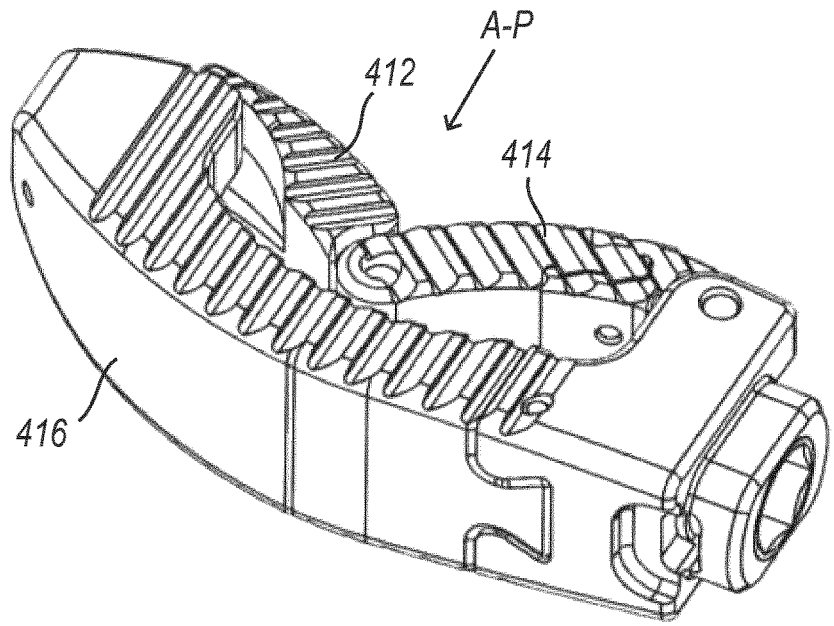
FIG. 27 is a perspective view of the device of FIG. 26 in a collapsed position according to one embodiment.
Figure 30:
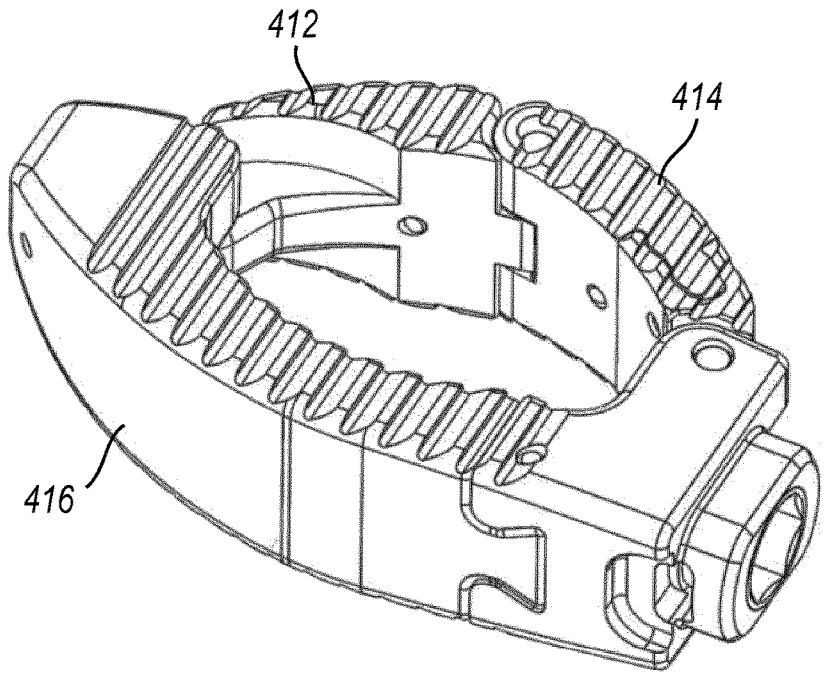
FIG. 30 is a perspective view of the device of FIG. 26 in an expanded position according to one embodiment.

In one embodiment, adjustment portion 418 enables user manipulation of device 410 to move device 410 between different degrees of expansion. Adjustment portion 418 may form a housing for device 410, and have a total length of approximately 13 mm. As shown in FIGS. 27 and 30, an end portion of adjustment portion 418 may extend beyond the top and bottom surfaces of device 410 (e.g., to an extent of approximately 3 mm, etc.). Pivot pin 424 indicates the general central portion of device 410, and thus facilitates ensuring that device 410 is properly centered in position. In some applications, pivot pin 424 is generally aligned with the spinous process when device 410 is installed. Locator pin 428 in some embodiments acts as a contralateral marker, indicating the contralateral position of device 410. In some applications, locator pin 428 is positioned approximately 2 mm from the extent of the contralateral position of device 410.

Pivot pins 424 and 426 and locator pin 428 in some embodiments provide an indication of the positioning of device 410 within a patient. Adjustment portion 418 may also provide an indication of the location of device 410. For example, these components may be radiographic elements such that images are generated by an imaging device (e.g., an x-ray device) and provide an indication of the positioning of device 410 within a patient. In combination with gauge pins 420, 422, adjustment portion 418, pivot pins 424, 426, and locator pin 428 enable generation of a visual indication of the position and degree of expansion of device 410 within a patient.

Figure 28:
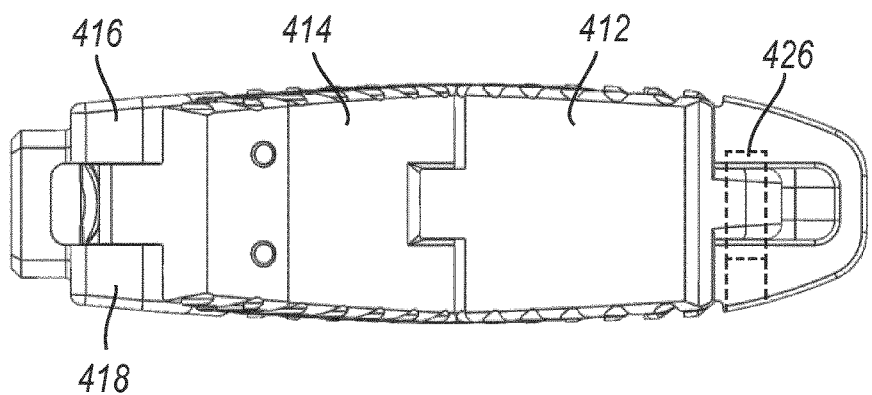
FIG. 28 is a side view of the device of FIG. 26 in a collapsed position according to one embodiment.
Figure 29:
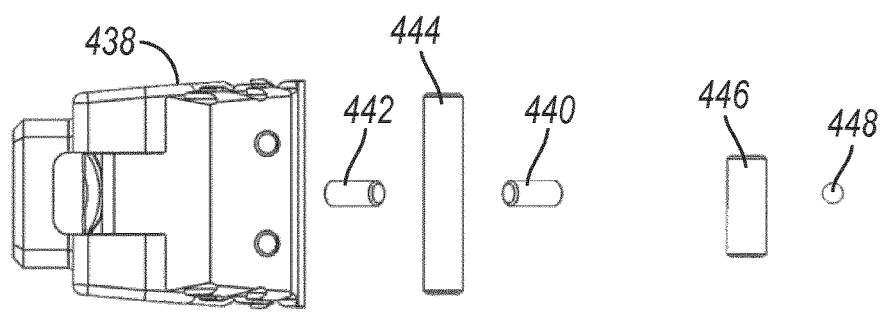
FIG. 29 is an image taken of the device of FIG. 26 in a collapsed position according to one embodiment.
Figure 31:
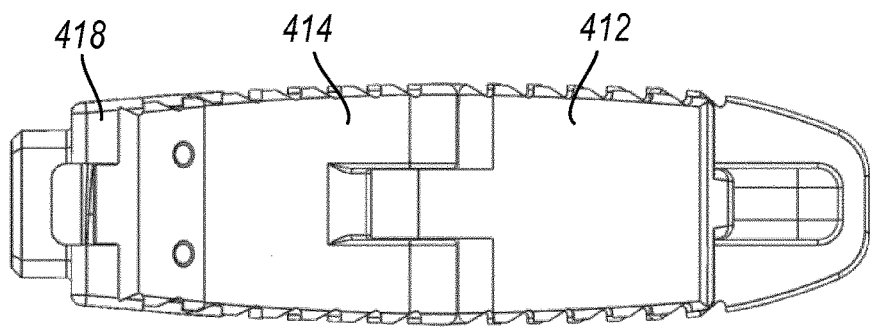
FIG. 31 is a side view of the device of FIG. 26 in an expanded position according to one embodiment.
Figure 32:
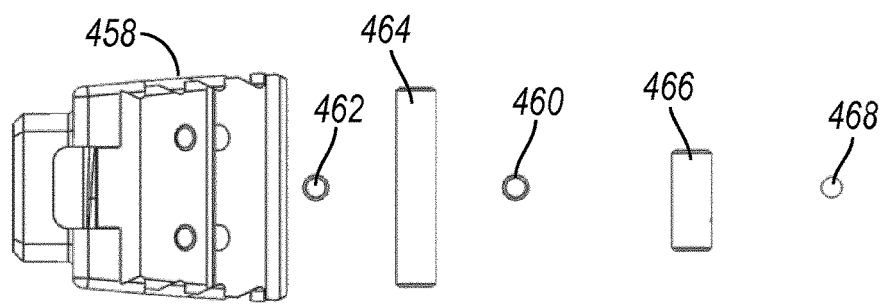
FIG. 32 is an image taken of the device of FIG. 26 in an expanded position according to one embodiment.

For example, referring to FIGS. 27-29, device 410 is in a collapsed position. FIG. 28 illustrates device 410 in a possible implanted position, and FIG. 29 illustrates an x-ray image of device 410 taken directed at the side of device 410 shown in FIG. 28 (e.g., along an anterior-posterior (A-P) direction shown by the arrow in FIG. 27). As shown in FIG. 29, outlines of adjustment portion 418 (image portion 438), gauge pins 420, 422 (image portions 440, 442), pivot pins 424, 426 (image portions 444, 446), and locator pin 428 (image portion 448) are all visible on the image reflecting the collapsed position of device 410. Referring to FIGS. 30-32, device 410 is in an expanded position. FIG. 31 illustrates device 410 in a possible implanted position, and FIG. 32 illustrates an x-ray image of device 410 taken directed at the side of device 410 shown in FIG. 31 (e.g., along an anterior-posterior direction). As shown in FIG. 32, outlines of adjustment portion 418 (image portion 458), gauge pins 420, 422 (image portions 460, 462), pivot pins 424, 426 (image portions 464, 466), and locator pin 428 (image portion 468) are all visible on the image reflecting the expanded position of device 410.

In one embodiment, one or more of the imaging elements provide an indicator for the degree of expansion of device 410. For example, in some embodiments, gauge pins 420, 422 are shaped and/or positioned within device 410 such that as device 410 is expanded within a patient, the x-ray view of gauge pins 420, 422 changes (e.g., the image of the gauge pins becomes longer/shorter). As shown in FIG. 29, in the fully collapsed position of device 410, gauge pins 420, 422 appear to be elongated elements having a first length, as shown by image portions 440, 442. As shown in FIG. 32, in the fully expanded position of device 410, gauge pins 420, 422 appear to be generally circular, as gauge pins 420, 422 become generally aligned lengthwise with the direction of imaging, as shown by image portions 460, 462. As such, the image portions corresponding to the gauge pins provide an indication of the degree of expansion of device 410, and appropriate look-up tables, algorithms, etc. may be used to determine intermediate degrees of expansion based on intermediate image portions.

In use, a user may insert device 410 into a desired position while in a collapsed position (see FIG. 28). During insertion, an imaging device such as an x-ray device may be oriented or directed at a side or other predetermined portion of device 410 to provide an x-ray image of certain components of device 410 (see FIG. 33). Once in a desired position, device 410 may be expanded/collapsed to desired expanded position. In order to gauge the degree of expansion, image portions corresponding to various image elements of device 410 may be viewed by way of a display device coupled to the imaging device to determine a current degree of expansion of device 410. Further adjustments and measurements of device 410 may be made until a desired degree of expansion is attained.

Figure 33:
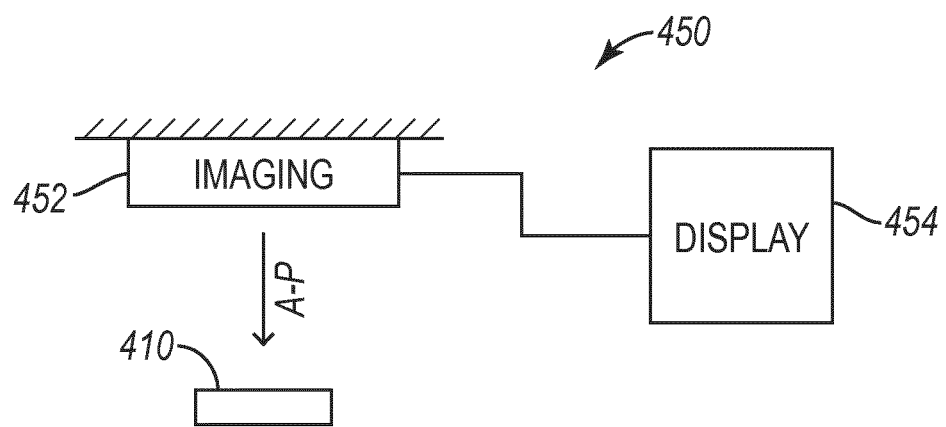
FIG. 33 is a schematic representation of an imaging system for use with a spinal interbody device according to one embodiment.

Referring to FIG. 33, a system 450 for acquiring one or more images of device 410 is shown according to one embodiment. System 450 includes an imaging device 452 and a display device 454. Imaging device 452 is configured to acquire one or more images of device 410, for example, during insertion or adjustment of device 410 within a patient. Imaging device 452 is operatively coupled to display device 454. Images acquired by imaging device 452 are displayed on display device 454 (e.g., such as the images shown in FIGS. 29 and 32). In one embodiment, imaging device 452 is an x-ray imaging device. In other embodiments, other imaging devices may be used.

Figure 34:
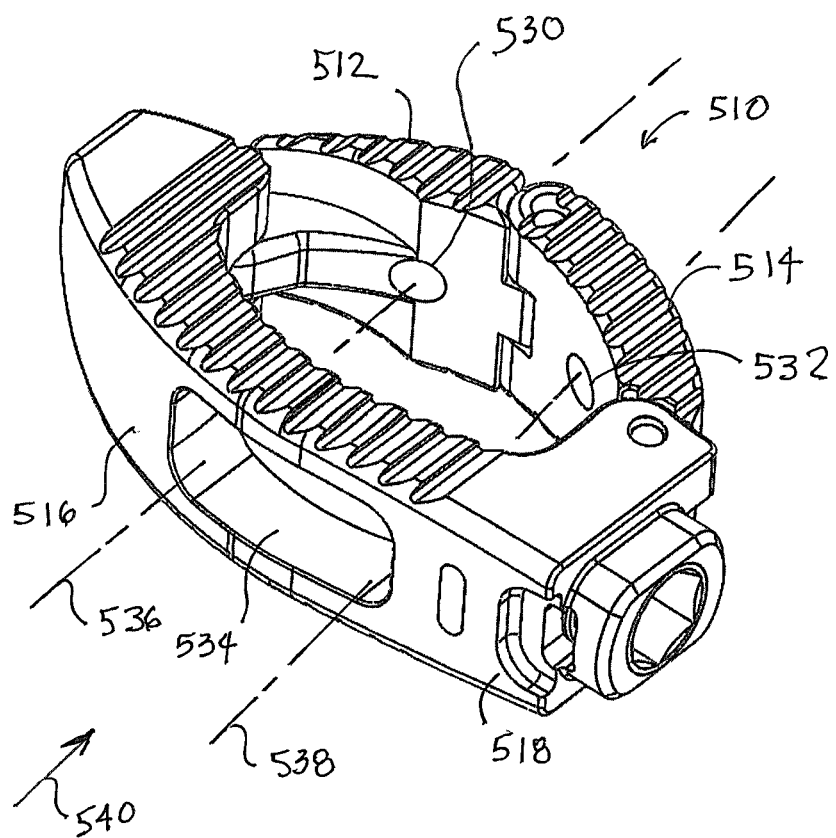
FIG. 34 is a perspective view of an interbody device in an expanded position according to another embodiment.
Figure 35:
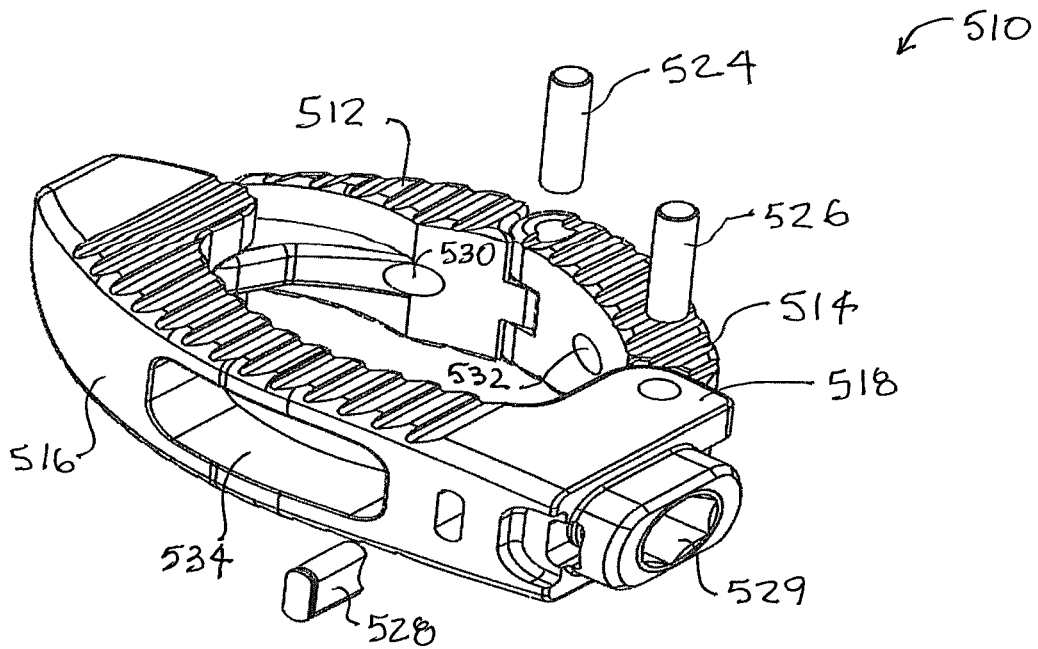
FIG. 35 is a partially exploded view of the interbody device of FIG. 34 according to one embodiment.

Referring now to FIGS. 34-39, a spinal interbody device 510 is shown according to an exemplary embodiment. As shown in FIGS. 34-35, device 510 includes a first link 512, a second link 514, and a third or base link 516. Third link 516 includes adjustment portion 518, which includes adjustment features to facilitate expansion/contraction of device 510. Device 510 includes adjustment end 518, pivot pins 524, 526, and retention element 528. Pivot pins 524, 526 enable relative movement of first link 512, second link 514, and base link 516. Retention element 528 is usable to retain adjustment member 529 in place during use of device 510. Device 510 can be moved from a first, radially collapsed, or retracted configuration, (similar to that shown in FIG. 37), to a second, or radially expanded configuration (similar to that shown in FIGS. 34-35). Similar to devices 10, 210, 310, and 410, device 510 is implantable between adjacent portions of bone, such as vertebrae, in a radially collapsed configuration and, once in proper position, is expandable through and up to a maximum radially expanded position. Device 510 is substantially the same as devices 310 and 410, with the exception of the imaging features and components (e.g., voids, cutouts, or apertures, etc.) and placement thereof discussed in greater detail below, and as such may share many features of devices 310 and 410. All such combinations of features are understood to be within the scope of the present disclosure.

In one embodiment, device 510 includes one or more apertures (e.g., elements such as voids, through-holes, etc. viewable with an imaging device such as an x-ray, etc.) configured to facilitate insertion and adjustment of device 510. For example, referring to FIGS. 34-39, device 510 includes a first aperture 530, a second aperture 532, and a cutout 534. The remaining portions of device 510 may be made of a radiographic material, such that when viewed from a lateral side of device 510 (e.g., along arrow 540) voids that extend fully through device 510 appear as relatively lighter image portions relative to radiographic portions.

In one embodiment, first aperture 530 extends fully through first link 512, second aperture 532 extends fully through second link 514, and cutout 534 extends fully through base link 516. First aperture 530, second aperture 532, and cutout 534 all extend along axes parallel to axis or arrow 540 shown in FIG. 34. In some embodiments, axis 540 extends generally perpendicular to the longitudinal length of device 510. As such, when device 510 is in an open position, cutout 534, first aperture 530, and second aperture 532 provide a line of sight through device 510 that is unobstructed by the structure of device 510.

Figure 36:
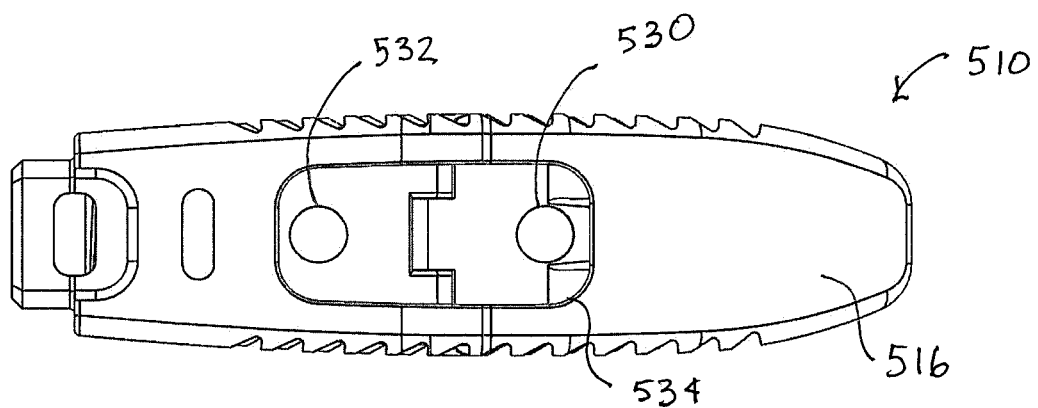
FIG. 36 is a side view of the interbody device of FIG. 34 in the expanded position according to one embodiment.
Figure 38:
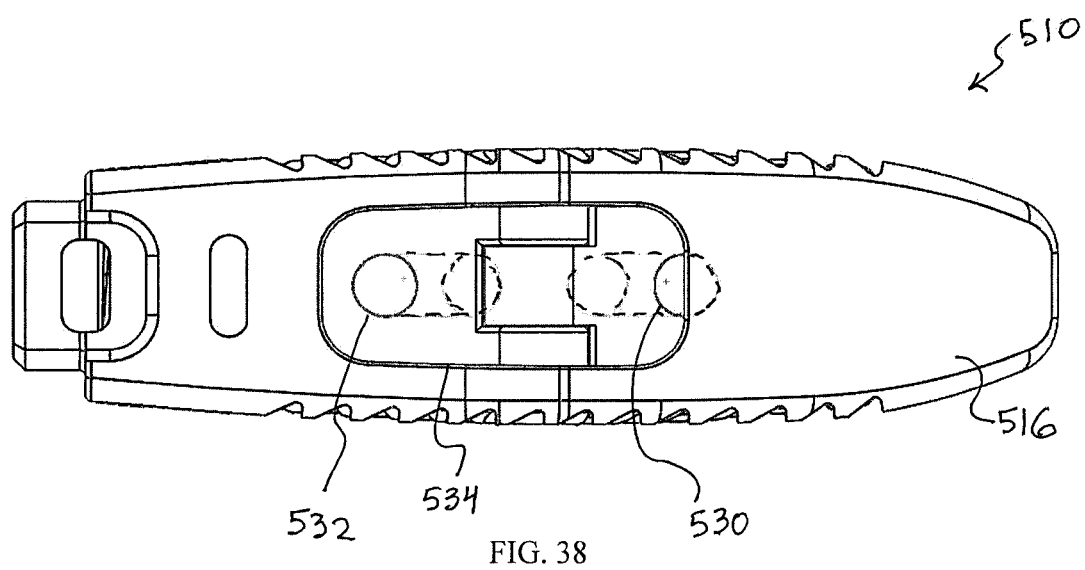
FIG. 38 is a side view of the interbody device of FIG. 34 in the collapsed position according to one embodiment.

FIG. 36 shows device 510 in an expanded position such that an unobstructed line of sight extends through cutout 534 and both of first apertures 530, 532. In contrast, FIG. 38 shows device 510 is a collapsed position, such that when viewed through cutout 534, the axes of apertures 530 and 532 are skewed such that no line of sight extends through the entirety of device 510. As such, when viewed with an imaging device along axis 540 shown in FIG. 34, device 510 in the open position would result in an image including two relatively lighter circular image portions representing apertures 530, 532, with the remainder of device 510 appearing relatively darker. Device 510 in the collapsed position would not include these image portions, but would rather show device 510 as being substantially opaque. At intermediate positions of device 510, any of the image portions of FIG. 39 (or others) may appear.

In some embodiments, device 510 is made fully or substantially from a metal (e.g., a radiographic material), such as titanium. As a result, when device 510 is viewed from a perspective along axis 540, first and second apertures 530, 532 will be viewable (e.g., appear as voids or lighter image portions) on an imaging screen due to the lack of radiographic material and the lack of structure in this area.

In one embodiment apertures 530, 532 are elongated and cylindrical in shape. In other embodiments, other shapes may be used. Apertures 530, 532 are positioned in device 510 such that as device 510 is expanded or collapsed, an image portion (e.g., an x-ray image) generated from a predetermined perspective relative to device 510 changes in shape. In some embodiments, a full circle gradually appears (due to the lack of radiographic material) as device 10 is expanded, thereby providing a visual indication of the degree of expansion of device 510.

Figure 39:
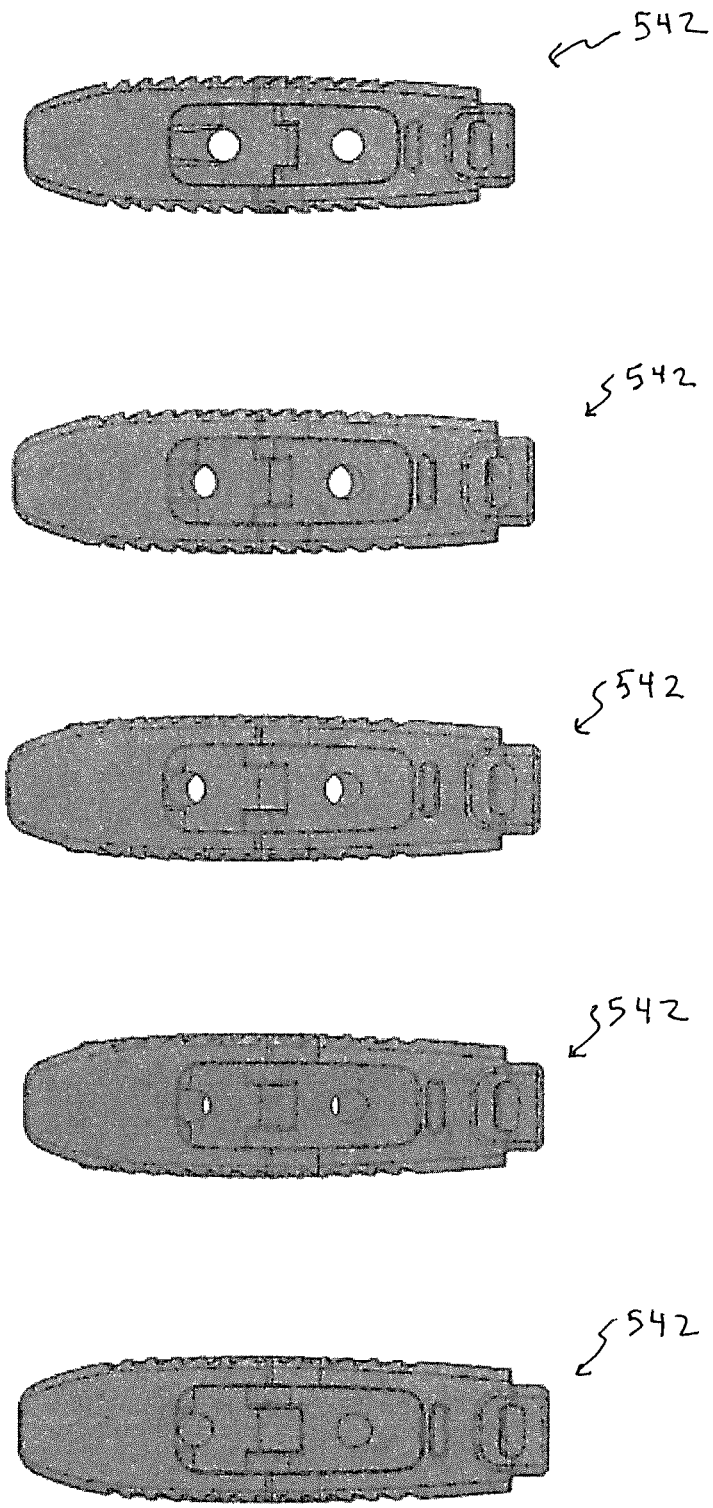
FIG. 39 is a schematic representation of a sequence of imaging views or portions taken during reconfiguration of the interbody device of FIG. 34 between a collapsed position and an expanded position according to one embodiment.

For example, FIG. 39 includes a series of image portions 542 that may be generated by an imaging device situated at a perspective along axis 540. FIG. 39 represents reconfiguration of device 510 from a collapsed position to an expanded position. The void image portions resulting from first and second apertures 530, 532 only appear when there is a lack of radiographic structure along, for example the direction of imaging, in this case along axis 540. The images of FIG. 39 represent reconfiguration of a device between a collapsed position (see bottom image) and an expanded position (see top image). Due to the orientation of first and second apertures 530, 532, when in a collapsed position, no void image portion is viewable, as shown in the bottom image of FIG. 39. As device 510 is moved from the collapsed position to the expanded position, the cross sectional area of the unobstructed view through device 510 increases and approaches a circle, as shown in the top image of FIG. 39.

In one embodiment, adjustment portion 518 enables user manipulation of device 510 to move device 510 between different degrees of expansion. Apertures 530, 532 and cutout 534 in some embodiments provide an indication of the location and/or degree of expansion of device 510 within a patient. For example, in the case where device 510 is made of a metal such as titanium, apertures 530, 532 and cutout 534 may appear as voids in certain configurations of device 510 when images are generated by an imaging device (e.g., an x-ray device) and provide an indication of the positioning of device 510 within a patient. In combination with cutout 534, first and second apertures 530, 532 enable generation of a visual indication of the position and degree of expansion of device 510 within a patient.

Figure 37:
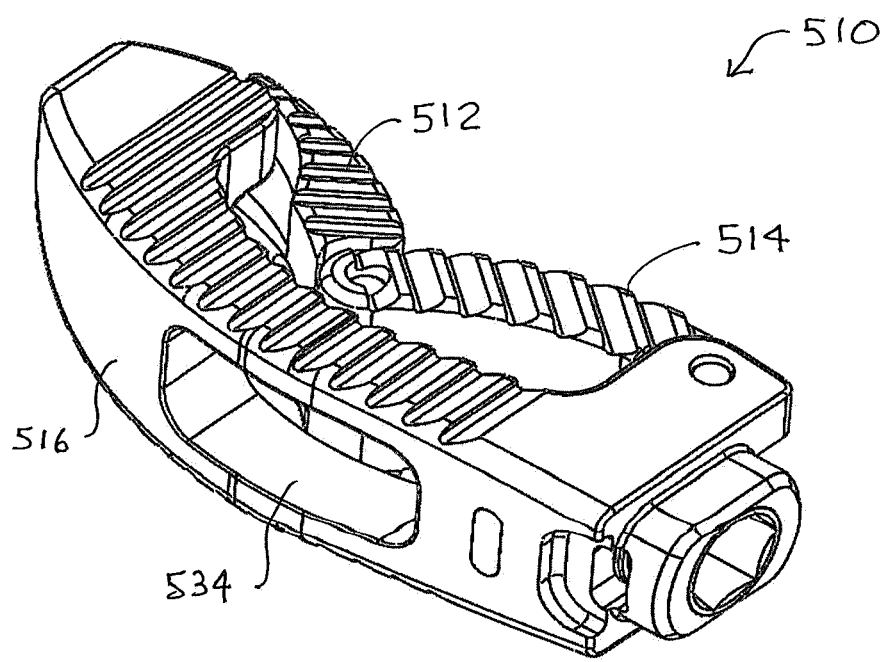
FIG. 37 is a perspective view of the interbody device of FIG. 34 in a collapsed position according to one embodiment.

In use, a user may insert device 510 into a desired position while in a collapsed position (see FIG. 37). During insertion, an imaging device such as an x-ray device may be oriented or directed at a side or other predetermined portion of device 510 to provide an x-ray image of certain components of device 510. Once in a desired position, device 510 may be expanded/collapsed to desired expanded position. In order to gauge the degree of expansion, image portions corresponding to various image elements of device 510 may be viewed by way of a display device coupled to the imaging device to determine a current degree of expansion of device 510 (see FIG. 39). Device 510 is usable with system 450 for acquiring one or more images of device 510 is shown according to one embodiment. In other embodiments, other imaging devices may be used.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. An expandable implant comprising:
   a base link comprising a first end, a second end, and a base link aperture extending through the base link from a first side of the base link to a second side of the base link, the first side of the base link being on a first side of the implant;
   a first link comprising a first end coupled to the first end of the base link, a second end, and a first link aperture extending from a first side of the first link to a second side of the first link, the second side of the first link being on a second side of the implant; and
   a second link comprising a first end coupled to the second end of the first link, a second end coupled to the second end of the base link, and a second link aperture extending from a first side of the second link to a second side of the second link, the second side of the second link being on the second side of the implant;
   wherein when the implant is in an expanded configuration, a first line of sight is provided through the base link aperture and the first link aperture from the first side of the implant to the second side of the implant, and a second line of sight is provided through the base link aperture and the second link aperture from the first side of the implant to the second side of the implant.

2. The expandable implant of claim 1, wherein when the implant is in a fully collapsed configuration, no line of sight is provided through the base link aperture and the first link aperture from the first side of the implant to the second side of the implant, and no line of sight is provided through the base link aperture and the second link aperture from the first side of the implant to the second side of the implant.

3. The expandable implant of claim 1, wherein the base link, the first link, and the second link are configured such that as the expandable implant is moved from a collapsed position to an expanded position, a first cross-sectional area of the first line of sight changes and a second cross-sectional area of the second line of sight varies.

4. The expandable implant of claim 3, wherein the base link, the first link, and the second link are made of a radiographic material.

5. The expandable implant of claim 1, wherein at least one of the first link aperture and the second link aperture is cylindrical in shape.

6. The expandable implant of claim 1, wherein the first end of the base link comprises a slot; and
   wherein the first end of the first link defines a pivot point, wherein the first link pivots about the pivot point and the pivot point translates along a path defined by the slot.

7. The expandable implant of claim 1, further comprising an adjustment member received by the base link; wherein manipulation of the adjustment member causes the expandable implant to move between a collapsed configuration and the expanded configuration.

8. The expandable implant of claim 7, wherein the second end of the second link comprises a plurality of gears configured to engage the adjustment member, wherein rotation of the adjustment member causes the expandable implant to move between the collapsed configuration and the expanded configuration.

9. A method of implanting an expandable device, comprising:
   positioning an expandable device in a desired location, the expandable device comprising a base link comprising a base link void and a first link comprising a first link void;
   positioning an imaging device at a predetermined orientation relative to the expandable device;
   adjusting the expandable device to a first degree of expansion;
   acquiring an image portion using the imaging device, the image portion resulting from a first line of sight existing from the imaging device through the base link void and through the first link void;
   determining a degree of expansion of the expandable device based on the image portion; and
   adjusting the expandable device to a second degree of expansion.

10. The method of claim 9, wherein the expandable device further comprises a second link comprising a second link void, and wherein the image portion further resulting from a second line of sight existing from the imaging device through the base link void and through the second link void.

11. The method of claim 9, further comprising positioning the expandable device and the imaging device relative to one another such that as the expandable device is adjusted, the image portion acquired by the imaging device and resulting from the first line of sight changes in shape.

12. The method of claim 9, wherein the expandable device further comprises a second link, wherein a first end of the first link is coupled to a first end of the base link, a second end of the first link is pivotally coupled to a first end of the second link, and a second end of the second link is coupled to a second end of the base link.

13. The method of claim 12, wherein the first end of the base link comprises a slot;
   wherein the first end of the first link pivots about a pivot point; and
   wherein the pivot point translates along a path defined by the slot.

14. The method of claim 9, wherein the expandable device further comprises:
   an adjustment member received by the base link, wherein manipulation of the adjustment member causes the expandable device to move between a collapsed configuration and an expanded configuration; and
   a second link, wherein a second end of the second link comprises a plurality of gears configured to engage the adjustment member, wherein rotation of the adjustment member causes the expandable device to move between the collapsed configuration and the expanded configuration.

15. An expandable implant comprising:
   a base link comprising a first end, a second end, and a base link aperture positioned between the first end of the base link and the second end of the base link and extending through the base link from a first side of the base link to a second side of the base link, the first side of the base link being on a first side of the implant;
   a first link comprising a first end coupled to the first end of the base link, a second end, and a first link aperture positioned between the first end of the first link and the second end of the first link and extending from a first side of the first link to a second side of the first link, the second side of the first link being on a second side of the implant;
   a second link comprising a first end coupled to the second end of the first link, a second end coupled to the second end of the base link, and a second link aperture positioned between the first end of the second link and the second end of the second link and extending from a first side of the second link to a second side of the second link, the second side of the second link being on the second side of the implant;
   wherein when the implant is in an expanded configuration, a first axis extends through the base link aperture from the first side of the base link to the second side of the base link and the first link aperture from the first side of the first link to the second side of the first link, and a second axis extends through the base link aperture from the first side of the base link to the second side of the base link and the second link aperture from the first side of the second link to the second side of the second link.

16. The expandable implant of claim 15, wherein the first link aperture and the second link aperture are cylindrical in shape.

17. The expandable implant of claim 15, wherein the base link, the first link, and the second link are made of radiographic material.

18. The expandable implant of claim 15, wherein the first axis is generally parallel to the second axis when the implant is in the expanded configuration.

19. The expandable implant of claim 15, wherein the first end of the base link comprises a slot; and
   wherein the first end of the first link defines a pivot point, wherein the first link pivots about the pivot point and the pivot point translates along a path defined by the slot.

20. The expandable implant of claim 15, further comprising an adjustment member received by the base link; wherein manipulation of the adjustment member causes the expandable implant to move between a collapsed configuration and the expanded configuration;
   wherein the second end of the second link comprises a plurality of gears configured to engage the adjustment member, wherein rotation of the adjustment member causes the expandable implant to move between the collapsed configuration and the expanded configuration.

* * * * *